United States Patent
Nishino et al.

(10) Patent No.: US 10,413,546 B2
(45) Date of Patent: Sep. 17, 2019

(54) DRUG FOR PREVENTING AND/OR TREATING DEMENTIA

(71) Applicants: NATIONAL UNIVERSITY CORPORATION TOTTORI UNIVERSITY, Tottori (JP); NIPPON MEDICAL SCHOOL FOUNDATION, Tokyo (JP); NIPPON CHEMIPHAR CO., LTD., Tokyo (JP)

(72) Inventors: Takeshi Nishino, Tokyo (JP); Shinsuke Kato, Tottori (JP); Masako Kato, Tottori (JP); Hidenori Suzuki, Tokyo (JP); Ken Okamoto, Tokyo (JP)

(73) Assignees: NATIONAL UNIVERSITY CORPORATION TOTTORI UNIVERSITY, Tottori (JP); NIPPON MEDICAL SCHOOL FOUNDATION, Tokyo (JP); NIPPON CHEMIPHAR CO., LTD., Tokyo (JP)

( * ) Notice: Subject to any disclaimer, the term of this patent is extended or adjusted under 35 U.S.C. 154(b) by 0 days.

(21) Appl. No.: 15/548,550

(22) PCT Filed: Feb. 23, 2016

(86) PCT No.: PCT/JP2016/055226
§ 371 (c)(1),
(2) Date: Dec. 19, 2017

(87) PCT Pub. No.: WO2016/136727
PCT Pub. Date: Sep. 1, 2016

(65) Prior Publication Data
US 2018/0117047 A1 May 3, 2018

(30) Foreign Application Priority Data
Feb. 24, 2015 (JP) .................................. 2015-034426

(51) Int. Cl.
| A61K 31/519 | (2006.01) |
| A61K 31/437 | (2006.01) |
| A61K 31/4365 | (2006.01) |
| A61K 31/4355 | (2006.01) |
| A61P 25/28 | (2006.01) |
| A61K 31/403 | (2006.01) |
| A61K 31/4184 | (2006.01) |
| A61K 31/423 | (2006.01) |
| A61K 31/428 | (2006.01) |

(52) U.S. Cl.
CPC .......... *A61K 31/519* (2013.01); *A61K 31/403* (2013.01); *A61K 31/4184* (2013.01); *A61K 31/423* (2013.01); *A61K 31/428* (2013.01); *A61K 31/437* (2013.01); *A61K 31/4355* (2013.01); *A61K 31/4365* (2013.01); *A61P 25/28* (2018.01)

(58) Field of Classification Search
None
See application file for complete search history.

(56) References Cited

U.S. PATENT DOCUMENTS

| 2005/0239807 A1* | 10/2005 | Stamler ................ A61K 31/519 514/262.1 |
| 2006/0046968 A1 | 3/2006 | Elmarakby et al. |
| 2007/0293512 A1 | 12/2007 | Yoshida et al. |
| 2010/0240580 A1 | 9/2010 | Zoller et al. |
| 2011/0171739 A1 | 7/2011 | Kemp et al. |

FOREIGN PATENT DOCUMENTS

| EP | 1452528 A1 | 9/2004 |
| EP | 1911760 A1 | 4/2008 |
| EP | 2560008 A2 | 2/2013 |
| JP | 2706037 B2 | 1/1998 |
| JP | 2725886 B2 | 3/1998 |
| JP | 3202607 B2 | 8/2001 |
| JP | 2003201255 A | 7/2003 |
| JP | 3600832 B2 | 12/2004 |
| JP | 2005041802 A | 2/2005 |
| JP | 3779725 B2 | 5/2006 |
| JP | 2007533751 A | 11/2007 |
| JP | 2008510827 A | 4/2008 |
| JP | 2010536811 A | 12/2010 |

(Continued)

OTHER PUBLICATIONS

Alzheimer's Association. Prevention and Risk of Alzheimer's and Dementia. (2018) Web <https://www.alz.org/research/science/alzheimers_prevention_and_risk.asp>.*
The Alzhimer's Association. Types of Dementia (2018) Web <https://www.alz.org/dementia/types-of-dementia.asp>.*
Byrn, Stephen. Solid-State Chemistry of Drugs, 2nd Ed. (1999), Ch. 11 Hydrates and Solvates, 233-247.*
Morissette, Sherry. Adv. Drug Delivery Rev. 2004, 56, 275-300.*
Rouhi, A. Maureen. Chem. & Eng. News, (2003), 81(8), 32-35.*
BrainFocus Foundation. Amyloid Plaques and Neurofibrillary Tangles. (2017) Web < https://www.brightfocus.org/alzheimers/infographic/amyloid-plaques-and-neurofibrillary-tangles>.*

(Continued)

*Primary Examiner* — Emily A Bernhardt
*Assistant Examiner* — Laura M Daniel
(74) *Attorney, Agent, or Firm* — Greenblum & Bernstein, P.L.C.

(57) ABSTRACT

A medicament for prophylactic and/or therapeutic treatment of dementia, which comprises a compound represented by the formula (I) having a xanthine oxidase inhibitory action as an active ingredient.

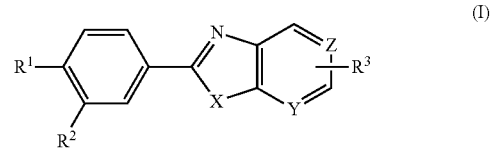

26 Claims, 10 Drawing Sheets

(56) References Cited

FOREIGN PATENT DOCUMENTS

| JP | 2012502966 A | 2/2012 | | |
|----|----|----|----|----|
| WO | 200342185 A1 | 5/2003 | | |
| WO | 2005121153 A1 | 12/2005 | | |
| WO | WO-2006026316 A2 * | 3/2006 | ........... | C07D 263/57 |
| WO | WO-2014083327 A1 * | 6/2014 | ........... | C07D 473/34 |

OTHER PUBLICATIONS

Jack CR et al., (2010) Progress of Alzheimer disease. Lancet neurol. 9., 2010, 119.
Journal of the American Chemical Society (1956), 784-790, 78.
Journal of the Chemical Society (1958), 2973-2981.
Bulletin des Travaux de la Societe de Pharmacie de Bordeaux (1928), 8-12, 66.
Berichte der Deutschen Chemischen Gesellschaft (1911), 2155-2158, 44.
Von Deutsch, Daniel A et al., FASEB Journal (2004), 18, 4-5, p. A933, 617.6.
Huang et al., Society for Neuroscience Abstracts (2001), 27, 2, p. 1521, 584.13.
Shirole et al., Clinical Therapeutics (2013), 35, 8, p. e100, pp. 264.
Alpan et al., Bioorganic & Medicinal Chemistry (2013), 21, 17, p. 4928-4937.
International Search Report from Application No. PCT/JP2016/055226 dated May 10, 2016.
International Preliminary Report on Patentability from Application No. PCT/JP2016/055226 dated Sep. 8, 2017.
Written Opinion of the International Searching Authority from Application No. PCT/JP2016/055226 dated Oct. 5, 2016.
Supplementary European search report issued in the corresponding European patent application No. 16755471.6, dated Jul. 20, 2018.
XP-002782651, Database Accession No. NLM12490776 (Pubmed ID: 12490776) for Diogo et al. "Allopurinol for the treatment of aggressive behavior in patients with dementia," International Clinical Psychopharmacology, Jan. 2003, vol. 18, No. 1, pp. 53-55.
Takako Niikura et al. "V642I APP-Inducible Neuronal Cells: A Model System for Investigating Alzheimer's Disorders," Biochemical and Biophysical Research Communications, 2000, vol. 274, pp. 445-454.

* cited by examiner

Histopathological images of the central nervous system with Alzheimer disease

| Human Alzheimer's disease | | An Alzheimer's disease model mouse |
|---|---|---|
|  | Senile Plaque |  |
|  | Neurofibrillary Tangle |  |

DRUG FOR PREVENTING AND/OR TREATING DEMENTIA

TECHNICAL FIELD

The present invention relates to a medicament for prophylactic and/or therapeutic treatment of dementia.

BACKGROUND ART

In recent years, with the increase of the elderly people's ratio among social population, elderly people's dementia has become a social problem. Dementia is roughly classified into Alzheimer type dementia, cerebrovascular dementia, and dementia with Lewy bodies, and especially the Alzheimer type dementia, of which number of patients is large, and for which countermeasure is difficult, poses a problem.

Neurofibrillary tangles in the cerebrum and increase in senile plaques are considered to be the causes of Alzheimer type dementia (Jack C R et al. (2010) Progress of Alzheimer disease, Lancet Neurol., 9, 119, 2010).

In the brain, the limbic system bears an important role for memory, and especially the hippocampus and the mammillary body are important organs that govern memory.

Although acetylcholine esterase inhibitors such as donepezil, galanthamine, and rivastigmine, and memantine, which is an NMDA receptor antagonist, are clinically used so far for improving symptoms of Alzheimer type dementia, sufficient curative effect has not been obtained yet.

Other than those mentioned above, as clinical trials for Alzheimer type dementia, there have been conducted clinical trials of AN1792 (Elan Pharmaceuticals), which is an amyloid vaccine, atorvastatin (Pfizer), and simvastatin (Merck), which are HMG-CoA reductase inhibitors, Dimebon (Pfizer), which is an antihistamine, tarenflurbil (Myriad Genetics), which is an NSAID, phenserine (Axonyx), which is an acetylcholine esterase inhibitor, rosiglitazone (Glaxo SmithKline), which is a PPARγ agonist, tramiprosate (Neurochem), which is an amyloid β polymerization inhibitor, xaliproden (Sanofi), which is a serotonin 1A receptor agonist, bapineuzumab (Pfizer), which is an antibody directed to the N-terminus of β amyloid, solanezumab (Eli Lilly), which is a monoclonal antibody directed to a central portion of β amyloid as an epitope, semagacestat (Eli Lilly), which is an inhibitor of γ-secretase involved in the β amyloid protein synthesis, and so forth. However, all of these could not exhibit any usefulness for the Alzheimer type dementia due to problems concerning validity or side reaction.

At present, there are being developed AZD3293 (AstraZeneca, Eli Lilly), which is an inhibitor of β secretase involved in the β amyloid protein synthesis, LuAE58054 (Lundbeck, Otsuka Pharmaceutical), which is a serotonin 5-HT6 receptor antagonist, and LuAF20513 (Lundbeck, Otsuka Pharmaceutical), which is a peptide vaccine of β amyloid. However, success of these is not guaranteed at all, in view of the fact that clinical developments of almost all the medicaments for Alzheimer's disease ended in failure.

Xanthine oxidase inhibitors such as allopurinol (Journal of the American Chemical Society (1956), 78, 784-90; Journal of the Chemical Society (1958), 2973-81), oxypurinol (Bulletin des Travaux de la Societe de Pharmacie de Bordeaux (1928) 66, 8-12; Berichte der Deutschen Chemischen Gesellschaft (1911), 44, 2155-8), febuxostat (Japanese Patent Nos. 2725886, 2706037, and 3202607), and topiroxostat (Japanese Patent Nos. 3600832, 3779725, and Japanese Patent Unexamined Publication (KOKAI) No. 2005-041802) are medicaments generally considered to be useful for the therapeutic treatment of hyperuricemia. All of these substances are compounds obtained in the process of preparing xanthine derivatives.

As references describing the relation between the xanthine oxidase inhibitor and dementia, there are Japanese Patent Unexamined Publication (KOHYO) No. 2007-533751 and Japanese Patent Unexamined Publication (KOKAI) No. 2003-201255, and any other prior references have not been found.

Japanese Patent Unexamined Publication (KOHYO) No. 2007-533751 describes a method for treatment of an Alzheimer's disease patient with a reactive oxygen-generating enzyme inhibitor in claim 25, and exemplifies xanthine oxidase inhibitor as the reactive oxygen-generating enzyme inhibitor. However, this reference specifically discloses only effects of allopurinol and nitrated allopurinol on sarcomere length and systolic calcium transient, which are indices of contraction of isolated cardiac muscle cells derived from nNOS-deficient rats (Japanese Patent Unexamined Publication (KOHYO) No. 2007-533751, FIG. 1). In addition, there are described use thereof for therapeutic treatment of Alzheimer's disease together with uses for heart failure (claim 6), stable angina pectoris (claim 8), ischemic reperfusion injury (claim 10), sickle cell disease (claim 12), heart failure, skeletal muscle force reduction, and respiratory failure (claim 17), atherosclerosis (claim 20), Parkinson's disease (claim 22), diabetes-related pain of lower extremities (claim 27), ALS (claim 29), and asthma (claim 31), as if they are in the same category. Therefore, it is regarded that this reference only mentions the use for Alzheimer's disease as one of efficacies of omnipotent reactive oxygen-generating enzyme inhibitors. As descriptions concerning Alzheimer's disease, Japanese Patent Unexamined Publication (KOHYO) No. 2007-533751 describes in Working Example XI that "A 65-year old with Alzheimer's disease is begun on 300 mg/day nitrated allopurinol (16). His memory and cognitive functions are stabilized after 3 months". However, this description does not include any description concerning specific administration frequency or specific cognitive performance improvement index. In addition, this description is a so-called predictive statement described in the present tense, and this reference neither refers to the action mechanism, nor confirms even that nitrated allopurinol has the xanthine oxidase inhibitory activity. Therefore, the efficacy of reactive oxygen-generating enzyme inhibitors cannot be enlarged over use for Alzheimer's disease.

According to Japanese Patent Unexamined Publication (KOKAI) No. 2003-201255, there were prepared nerve cells obtained by stably overexpressing both the ecdysone receptor EcR and retinoid X receptor for raising the sensitivity of the foregoing receptor in cells of the F11 cell strain, which are fusion cells of rat primarily cultured nerve cells and mouse neuroblastomas, and further transforming the cells with a plasmid that expresses an N141I mutant of presenilin 2 as the catalytic subunit of the γ-secretase, which mutant is a mutant that causes familial Alzheimer's disease upon addition of ecdysone, and death of the nerve cells caused by addition of ecdysone was examined. As a result, the nerve cell death was suppressed by (1) simultaneous addition of 100 μM of oxypurinol as a xanthine oxidase inhibitor and 100 μM of acetyl-L-aspartyl-L-glutamyl-L-valyl-L-aspart-1-al as a caspase inhibitor, (2) simultaneous addition of 100 nM of (−)-4-hydroxy-8-(3-methoxy-4-phenylsulfinylphenyl)pyrazolo[1,5-a]-1,3,5-triazine sodium salt as a xanthine oxidase inhibitor and 100 μM of acetyl-L-aspartyl-L-glutamyl-L-valyl-L-aspart-1-al as a caspase inhibitor, and (3)

simultaneous addition of 100 μM of oxypurinol as a xanthine oxidase inhibitor and 300 μM of apocynin as a NADPH oxidase inhibitor, and therefore this reference proposes an agent for prophylactic and/or therapeutic treatment of Alzheimer's disease containing a xanthine oxidase inhibitor, and an NADPH oxidase inhibitor and/or a caspase inhibitor as active ingredients.

However, in Japanese Patent Unexamined Publication (KOKAI) No. 2003-201255, suppression of the nerve cell death is not observed at all with a xanthine oxidase inhibitor alone, and therefore it cannot be said that that is the effect of xanthine oxidase inhibitor alone. Further, Japanese Patent Unexamined Publication (KOKAI) No. 2003-201255 describes only results of investigations at cell level, and therefore it is completely unknown whether such an agent can prevent or improve degeneration or reduction of nerve cells in an individual of animal. Furthermore, it cannot be confirmed that such an agent can prevent degeneration of a part of the cerebrum responsible for the cognitive function, or can prevent degradation of actual cognitive function from the descriptions of Japanese Patent Unexamined Publication (KOKAI) No. 2003-201255, and therefore it is completely unknown whether a xanthine oxidase inhibitor can prevent and/or cure dementia.

Any other prior techniques referring to the relation between a xanthine oxidase inhibitor and dementia are not known. Therefore, any prior art that teaches use of a xanthine oxidase inhibitor alone for prophylactic and/or therapeutic treatment of degradation of cognitive function in dementia is not known.

International Patent Publications WO2003/42185 and WO2005/121153 disclose compounds having a xanthine oxidase inhibitory action, and teach that these compounds are useful as prophylactic or therapeutic agent for hyperuricemia and gout.

PRIOR ART REFERENCES

Patent Documents

Patent document 1: Japanese Patent Unexamined Publication (KOHYO) No. 2007-533751
Patent document 2: Japanese Patent Unexamined Publication (KOKAI) No. 2003-201255
Patent document 3: International Patent Publication WO2003/42185
Patent document 4: International Patent Publication WO2005/121153
Patent document 5: Japanese Patent No. 3600832
Patent document 6: Japanese Patent No. 2725886
Patent document 7: Japanese Patent No. 2706037
Patent document 8: Japanese Patent No. 3202607
Patent document 9: Japanese Patent No. 3779725
Patent document 10: Japanese Patent Unexamined Publication (KOKAI) No. 2005-041802

Non-Patent Documents

Non-patent document 1: Jack C R et al. (2010) Progress of Alzheimer disease, Lancet Neurol., 9. 119, 2010
Non-patent document 2: Journal of the American Chemical Society (1956), 78, 784-90
Non-patent document 3: Journal of the Chemical Society (1958), 2973-81
Non-patent document 4: Bulletin des Travaux de la Societe de Pharmacie de Bordeaux (1928), 66, 8-12
Non-patent document 5: Berichte der Deutschen Chemischen Gesellschaft (1911), 44, 2155-8

SUMMARY OF THE INVENTION

Object to be Achieved by the Invention

An object of the present invention is to provide a medicament for prophylactic and/or therapeutic treatment of dementia.

Means for Achieving the Object

As for the cause and pathological symptoms of Alzheimer's disease, both the pathological finding that amyloid senile plaques of which core protein is the amyloid β peptide (Aβ) excessively accumulate in the cerebrum, and the pathological finding that many neurofiblils of which core protein is the tau protein as one of the microtubule binding proteins appear are considered to be pathologically most important. On the basis of these pathological findings, there has been developed a double transgenic mouse that highly expresses both of a gene encoding 695 amino acids of the amyloid β (Aβ) precursor protein of human Alzheimer's disease and having a Sweden mutation, and a human tau protein gene having a mutation for substituting leucine for proline at the position 301 (P301L) by genetic engineering. In this Alzheimer's disease model double transgenic mouse, there is observed a pathological tissue image that human senile plaques and human neurofibrillary tangles appear, which never appear in a normal mouse.

In order to achieve the aforementioned object, the inventors of the present invention administered compounds represented by the following general formula (I), which are xanthine oxidase inhibitors generally considered to be useful for therapeutic treatment of hyperuricemia, to the aforementioned Alzheimer's disease model double transgenic mice over one year after one year passed from the birth, and performed histological examination. As a result, it was surprisingly found that the compounds significantly suppress the appearance of both senile plaques and neurofibrillary tangles in the Alzheimer's disease model double transgenic mice. On the basis of this finding, the inventors of the present invention confirmed that the aforementioned compounds are useful as an active ingredient of a medicament for prophylactic and/or therapeutic treatment of dementia, and accomplished the present invention.

The present invention encompasses the following inventions.

[A1] A medicament for prophylactic and/or therapeutic treatment of dementia, which comprises a compound represented by the following general formula (A), a tautomer or stereoisomer of the compound, or a pharmaceutically acceptable salt thereof, or a crystal or solvate thereof as an active ingredient:

[Formula 1]

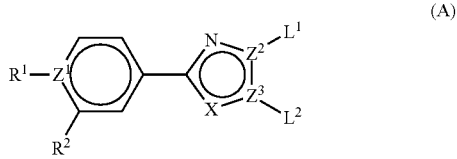

(wherein,

R¹ represents an alkyl group having 1 to 8 carbon atoms, an alkyl group having 1 to 8 carbon atoms and substituted with 1 to 3 halogen atoms, $OR^4$, $CO_2R^5$, $S(O)_nR^6$, or hydrogen atom, where $R^4$ represents hydrogen atom, or an alkyl group having 1 to 8 carbon atoms, aralkyl group (the aryl moiety has 6 to 10 carbon atoms, and the alkyl moiety has 1 to 4 carbon atoms), alkylcarbonyl group having 2 to 9 carbon atoms, arylcarbonyl group (the aryl moiety has 6 to 10 carbon atoms), aralkylcarbonyl group (the aryl moiety has 6 to 10 carbon atoms, and the alkylcarbonyl moiety has 2 to 5 carbon atoms), or aryl group having 6 to 10 carbon atoms, which may have a group or atom selected from a halogen atom, hydroxy group, nitro group, and cyano group as a substituent, $R^5$ and $R^6$ represent hydrogen atom, or an alkyl group having 1 to 8 carbon atoms, aralkyl group (the aryl moiety has 6 to 10 carbon atoms, and the alkyl moiety has 1 to 4 carbon atoms), or aryl group having 6 to 10 carbon atoms, which may have a group or atom selected from a halogen atom, hydroxy group, nitro group, cyano group, and amino group as a substituent, and n represents an integer of 0 to 2, $R^2$ represents hydrogen atom, a halogen atom, nitro group, cyano group, formyl group, an alkyl group having 1 to 8 carbon atoms, an alkyl group having 1 to 8 carbon atoms and substituted with 1 to 3 halogen atoms, or $CO_2R^7$, where $R^7$ has the same meaning as that of $R^5$ mentioned above, X represents carbon atom, nitrogen atom, oxygen atom, or sulfur atom, $Z^1$ represents carbon atom, or nitrogen atom, $Z^2$ and $Z^3$ independently represent carbon atom, nitrogen atom, or sulfur atom, $L^1$ and $L^2$ independently represent hydrogen atom, an alkyl group having 1 to 8 carbon atoms, an alkenyl group having 2 to 8 carbon atoms, an alkoxy group having 1 to 8 carbon atoms, an aryl group having 6 to 10 carbon atoms, or a heteroaryl group having 4 to 9 carbon atoms, or $L^1$ and $L^2$ may combine together to form a bicyclic heteroaryl ring together with the 5-membered ring to which they bond, and the bicyclic heteroaryl ring may be substituted with a halogen atom, hydroxy group, amino group, $CO_2R^8$, $PO_3H$, $PO(OH)(OR^9)$, $S(O)_mR^{10}$, or an alkyl group having 1 to 8 carbon atoms, or alkylaminocarbonyl group (the alkyl group has 1 to 8 carbon atoms), which may have a group or atom selected from a halogen atom, hydroxy group, nitro group, cyano group, and amino group as a substituent, where $R^8$, $R^9$, and $R^{10}$ has the same meaning as that of $R^5$ mentioned above, and m has the same meaning as that of n mentioned above).

[A2] The medicament according to [A1] mentioned above, wherein $Z^1$ is nitrogen atom, or carbon atom, and $R^1$ is $OR^4$ ($R^4$ is an alkyl group having 1 to 8 carbon atoms, or aryl group having 6 to 10 carbon atoms, which may have a group or atom selected from a halogen atom, hydroxy group, nitro group, and cyano group as a substituent), or hydrogen atom.

[A3] The medicament according to [A2] mentioned above, wherein $R^4$ is an alkyl group having 1 to 8 carbon atoms, or phenyl group.

[A4] The medicament according to any one of [A1] to [A3] mentioned above, wherein $R^2$ is nitro group, cyano group, a halogen atom, or carboxyl group.

[A5] The medicament according to [A4] mentioned above, wherein $R^2$ is cyano group.

[A6] The medicament according to any one of [A1] to [A5] mentioned above, wherein $Z^2$ is carbon atom, and $Z^3$ is carbon atom, or nitrogen atom.

[A7] The medicament according to any one of [A1] to [A6] mentioned above, wherein $L^1$ is an alkyl group having 1 to 8 carbon atoms, or a heteroaryl group having 4 to 9 carbon atoms, and $L^2$ is hydrogen atom, or an alkyl group having 1 to 8 carbon atoms.

[A6] The medicament according to any one of [A1] to [A7] mentioned above, wherein $L^1$ is phenyl group, 2-pyridyl group, 3-pyridyl group, 4-pyridyl group, 3-pyridazinyl group, 4-pyridazinyl group, 2-pyrimidinyl group, 4-pyrimidinyl group, or 5-pyrimidinyl group, and $L^2$ is hydrogen atom, methyl group, ethyl group, or propyl group, or $L^1$ and $L^2$ may combine together to form a bicyclic heteroaryl ring selected from thiazolo[5,4-d]pyrimidine, oxazolo[5,4-d]pyrimidine, 7H-pyrrolo[3,2-d]pyrimidine, 9H-purine, thiazolo[4,5-d]pyridazine, oxazolo[4,5-d]pyridazine, 7H-imidazo[4,5-d]pyridazine, thiazolo[5,4-c]pyridazine, oxazolo[5,4-c]pyridazine, 7H-imidazo[4,5-c]pyridazine, thiazolo[4,5-d]triazine, oxazolo[4,5-d]triazine, and 7H-imidazo[4,5-d]triazine together with the 5-membered ring to which they bond, and the bicyclic heteroaryl ring may be substituted with hydroxy group, or an alkyl group having 1 to 8 carbon atoms, which may have hydroxy group as a substituent.

[A9] The medicament according to any one of [A1] to [A6] mentioned above, wherein X is sulfur atom, or nitrogen atom.

[A10] The medicament according to any one of [A1] to [A9] mentioned above, wherein X is nitrogen atom, $Z^2$ is carbon atom, $L^1$ is 4-pyridyl group, $Z^3$ is nitrogen atom, and $L^2$ is hydrogen atom.

[A11] The medicament according to any one of [A1] to [A10] mentioned above, wherein X is sulfur atom, both $Z^2$ and $Z^3$ are carbon atoms, $L^1$ and $L^2$ may combine together to form a bicyclic heteroaryl ring selected from thiazolo[5,4-d]pyrimidine, oxazolo[5,4-d]pyrimidine, 7H-pyrrolo[3,2-d]pyrimidine, and 9H-purine, and the bicyclic heteroaryl ring may be substituted with hydroxy group.

[A12] Use of a compound represented by the general formula (A), a tautomer or stereoisomer of the compound, or a pharmaceutically acceptable salt thereof, or a crystal or solvate thereof mentioned in any one of [A1] to [A11] mentioned above for manufacture of the medicament according to any one of [A1] to [A11] mentioned above.

[A13] Use of a compound represented by the general formula (A), a tautomer or stereoisomer of the compound, or a pharmaceutically acceptable salt thereof, or a crystal or solvate thereof according to any one of [A1] to [A11] mentioned above for prophylactic and/or therapeutic treatment of dementia.

[A14] A method for prophylactic and/or therapeutic treatment of dementia in a human, which comprises the step of administering a prophylactically and/or therapeutically effective amount of a compound represented by the general formula (A), a tautomer or stereoisomer of the compound, or a pharmaceutically acceptable salt thereof or a crystal or solvate thereof according to any one of [A1] to [A11] mentioned above to the human.

[A15] Use of a compound represented by the general formula (A), a tautomer or stereoisomer of the compound, or a pharmaceutically acceptable salt thereof, or a crystal or solvate thereof mentioned in any one of [A1] to [A11] mentioned above for manufacture of a medicament for suppressing increase of number of large-sized senile plaques or medium-sized senile plaques, or number of nerve cells having neurofibrillary tangles, and/or decreasing the number.

[A16] The medicament, use, or method according to any one of [A1] to [A15] mentioned above, wherein the dementia is Alzheimer type dementia.

[B1] A medicament for prophylactic and/or therapeutic treatment of dementia, which comprises a compound represented by the following general formula (I), a tautomer or stereoisomer of the compound, or a pharmaceutically acceptable salt thereof or a crystal or solvate thereof as an active ingredient:

[Formula 2]

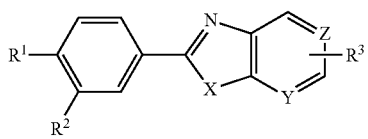

(I)

(wherein, $R^1$ represents an alkyl group having 1 to 8 carbon atoms, an alkyl group having 1 to 8 carbon atoms and substituted with 1 to 3 halogen atoms, —$OR^4$, —$CO_2R^5$, or —$S(O)_nR^6$, where $R^4$ represents hydrogen atom, or an alkyl group having 1 to 8 carbon atoms, aralkyl group (the aryl moiety has 6 to 10 carbon atoms, and the alkyl moiety has 1 to 4 carbon atoms), alkylcarbonyl group having 2 to 9 carbon atoms, arylcarbonyl group (the aryl moiety has 6 to 10 carbon atoms), aralkylcarbonyl group (the aryl moiety has 6 to 10 carbon atoms, and the alkylcarbonyl moiety has 2 to 5 carbon atoms), or aryl group having 6 to 10 carbon atoms, which may have a group or atom selected from a halogen atom, hydroxy group, nitro group, and cyano group as a substituent, $R^5$ and $R^6$ independently represent hydrogen atom, or an alkyl group having 1 to 8 carbon atoms, aralkyl group (the aryl moiety has 6 to 10 carbon atoms, and the alkyl moiety has 1 to 4 carbon atoms), or aryl group having 6 to 10 carbon atoms, which may have a group or atom selected from a halogen atom, hydroxy group, nitro group, cyano group, and amino group as a substituent, and n represents an integer of 0 to 2, $R^2$ represents hydrogen atom; a halogen atom, nitro group, cyano group, formyl group, an alkyl group having 1 to 8 carbon atoms, an alkyl group having 1 to 8 carbon atoms and substituted with 1 to 3 halogen atoms, or $CO_2R^7$, where $R^7$ has the same meaning as that of $R^5$ mentioned above, $R^3$ represents hydrogen atom, a halogen atom, hydroxy group, amino group, $CO_2R^8$, $PO_3H$, $PO(OH)(OR^9)$, $S(O)_mR^{10}$, or an alkyl group having 1 to 8 carbon atoms, or alkylaminocarbonyl group (the alkyl group has 1 to 8 carbon atoms), which may have a group or atom selected from a halogen atom, hydroxy group, nitro group, cyano group, and amino group as a substituent, where $R^8$, $R^9$, and $R^{10}$ have the same meaning as that of $R^5$ mentioned above, and m has the same meaning as that of n mentioned above, X represents $NR^{11}$, oxygen atom, or sulfur atom, where $R^{11}$ represents hydrogen atom, or an alkyl group having 1 to 8 carbon atoms, which may have a group or atom selected from a halogen atom, hydroxy group, nitro group, cyano group, and amino group as a substituent, and Y and Z represent $CR^{12}$ or nitrogen atom, where $R^{12}$ has the same meaning as that of $R^3$ mentioned above).

[B2] The medicament according to [B1] mentioned above, wherein $R^1$ is $OR^4$.

[B3] The medicament according to [B2] mentioned above, wherein $R^4$ is an alkyl group having 1 to 8 carbon atoms, or aryl group having 6 to 10 carbon atoms, which may have a substituent selected from the group consisting of a halogen atom, hydroxy group, nitro group, and cyano group.

[B4] The medicament according to [B1] or [B2] mentioned above, wherein $R^1$ is an alkoxy group having 1 to 5 carbon atoms, or phenoxy group, which may have a substituent selected from the group consisting of a halogen atom, hydroxy group, nitro group, and cyano group.

[B5] The medicament according to any one of [B1] to [B4] mentioned above, wherein $R^2$ is nitro group, cyano group, a halogen atom, or carboxyl group.

[B6] The medicament according to any one of [B1] to [B5] mentioned above, wherein $R^3$ is hydrogen atom, amino group, hydroxy group, a halogen atom, or carboxyl group.

[B7] The medicament according to any one of [B1] to [B6] mentioned above, wherein X is oxygen atom, or sulfur atom.

[B8] The medicament according to any one of [B1] to [B7] mentioned above, wherein both Y and Z are nitrogen atoms.

[B9] The medicament according to any one of [B1] to [B8] mentioned above, wherein $R^1$ is an alkoxy group having 1 to 5 carbon atoms, or phenoxy group, which may have a substituent selected from the group consisting of a halogen atom, hydroxy group, nitro group, and cyano group, $R^2$ is nitro group, cyano group, a halogen atom, or carboxyl group, $R^3$ is hydrogen atom, amino group, hydroxy group, a halogen atom, or carboxyl group, X is oxygen atom, or sulfur atom, and both Y and Z are nitrogen atoms.

[B10] The medicament according to any one of [B] to [B9] mentioned above, wherein $R^1$ is an alkoxy group having 1 to 5 carbon atoms, or phenoxy group, $R^2$ is cyano group, $R^3$ is hydroxy group, X is oxygen atom, or sulfur atom, and both Y and Z are nitrogen atoms.

[B11] A medicament comprising any one of the following compounds (1) to (30):

[Formula 3]

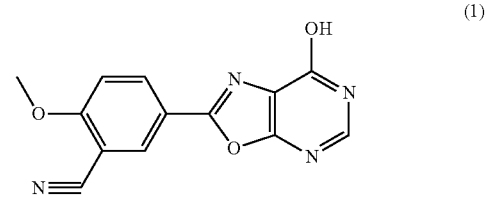

(1)

5-(7-hydroxyoxazolo[5,4-d]pyrimidin-2-yl)-2-methoxy-benzonitrile

[Formula 4]

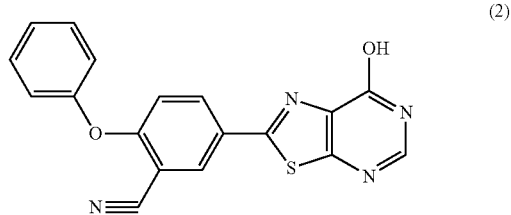

(2)

5-(7-hydroxythiazolo[5,4-d]pyrimidin-2-yl)-2-phenoxy-benzonitrile

[Formula 5]

(3)

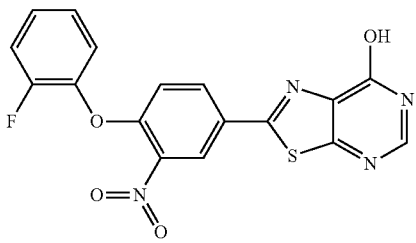

2-[4-(2-fluorophenoxy)-3-nitro-phenyl]thiazolo[5,4-d]pyrimidin-7-ol (4)

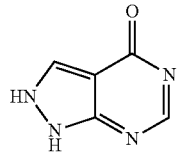

1,2-dihydropyrazolo[3,4-d]pyrimidin-4-one (5)

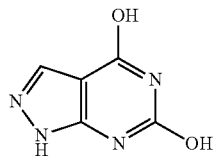

1H-pyrazolo[3,4-d]pyrimidine-4,6(5H,7H)-dione (6) 2-[4-(4-fluorophenoxy)-3-cyanophenyl]thiazolo[5,4-d]pyrimidine
(7) 2-(3-cyano-4-phenoxyphenyl)thiazolo[5,4-d]pyrimidine
(8) 2-[3-cyano-4-(3-pyridyloxy)phenyl]thiazolo[5,4-d]pyrimidine
(9) 8-[3-cyano-4-(4-fluorophenoxy)phenyl]-9H-purine
(10) 2-[3-cyano-4-(2-fluorophenoxy)phenyl]thiazolo[5,4-d]pyrimidine
(11) 2-[3-cyano-4-(3-fluorophenoxy)phenyl]thiazolo[5,4-d]pyrimidine
(12) 2-[3-cyano-4-(4-fluorophenylthio)phenyl]thiazolo[5,4-d]pyrimidine
(13) 2-[3-cyano-4-(2-hydroxyphenoxy)phenyl]thiazolo[5,4-d]pyrimidine
(14) 2-[4-(4-chlorophenyloxy)-3-cyanophenyl]thiazolo[5,4-d]pyrimidine
(15) 2-[3-cyano-4-(2-fluorophenylthio)phenyl]thiazolo[5,4-d]pyrimidine
(16) 2-(3-cyano-4-phenylthiophenyl)thiazolo[5,4-d]pyrimidine
(17) 2-(4-allyloxy-3-cyanophenyl)thiazolo[5,4-d]pyrimidine
(18) 2-(3-cyano-4-morpholin-4-ylphenyl)thiazolo[5,4-d]pyrimidine
(19) 2-[3-cyano-4-(4-methyl-1-piperazinyl)phenyl]thiazolo[5,4-d]pyrimidine
(20) 2-[4-(3-chlorophenyloxy)-3-cyanophenyl]thiazolo[5,4-d]pyrimidine
(21) 2-[3-cyano-4-(thiomorpholin-4-yl)phenyl]thiazolo[5,4-d]pyrimidine
(22) 2-[4-(2-chlorophenyloxy)-3-cyanophenyl]thiazolo[5,4-d]pyrimidine
(23) 2-[3-cyano-4-(4-fluorophenoxy)phenyl]oxazolo[5,4-d]pyrimidine
(24) 2-[3-cyano-4-(3-fluorophenylthio)phenyl]thiazolo[5,4-d]pyrimidine
(25) 2-[4-(2-aminophenoxy)-3-cyanophenyl]thiazolo[5,4-d]pyrimidine
(26) 2-[3-cyano-4-(3-pyridyloxy)phenyl]thiazolo[5,4-d]pyrimidine hydrochloride
(27) 2-[3-cyano-4-(4-hydroxyphenoxy)phenyl]thiazolo[5,4-d]pyrimidine
(28) 2-[3-cyano-4-(2-hydroxycarbonylphenoxy)phenyl]thiazolo[5,4-d]pyrimidine
(29) 2-[3-cyano-4-(2-hydroxyphenoxy)phenyl]thiazolo[5,4-d]pyrimidine potassium salt
(30) 2-[3-cyano-4-(4-hydroxyphenoxy)phenyl]thiazolo[5,4-d]pyrimidine potassium salt

[B12] Use of a compound represented by the general formula (I), a tautomer or stereoisomer of the compound, or a pharmaceutically acceptable salt thereof, or a crystal or solvate thereof mentioned in any one of [B1] to [B10] mentioned above for manufacture of the medicament according to any one of [B1] to [B11].

[B13] Use of a compound represented by the general formula (I), a tautomer or stereoisomer of the compound, or a pharmaceutically acceptable salt thereof, or a crystal or solvate thereof mentioned in any one of [B] to [B11] for prophylactic and/or therapeutic treatment of dementia.

[B14] A method for prophylactic and/or therapeutic treatment of dementia in a human, which comprises the step of administering a prophylactically and/or therapeutically effective amount of a compound represented by the general formula (I), a tautomer or stereoisomer of the compound, or a pharmaceutically acceptable salt thereof, or a crystal or solvate thereof mentioned in any one of [B1] to [B11] mentioned above to the human.

[B15] Use of a compound represented by the general formula (I), a tautomer or stereoisomer of the compound, or a pharmaceutically acceptable salt thereof, or a crystal or solvate thereof mentioned in any one of [B1] to [B11] mentioned above for manufacture of a medicament for suppressing increase of number of large-sized senile plaques or medium sized senile plaques, or number of nerve cells having neurofibrillary tangles, and/or decreasing the number.

[B16] The medicament, use, or method according to any one of [B1] to [B15] mentioned above, wherein the dementia is Alzheimer type dementia.

Effect of the Invention

Since the medicament of the present invention can markedly suppress emergence of both senile plaques and neurofibrillary tangles, it is useful as a medicament for prophylactic and/or therapeutic treatment of Alzheimer type dementia.

MODES FOR CARRYING OUT THE INVENTION

Figure 1:
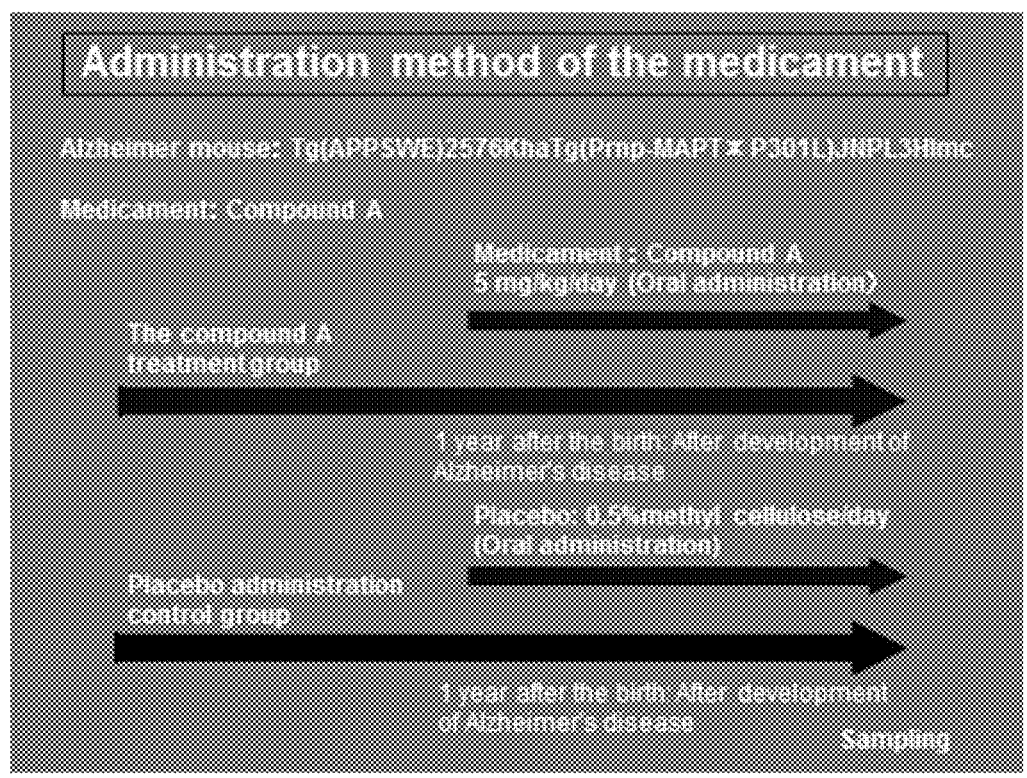
FIG. 1 A schematic diagram showing the protocol of administration of the medicament to the Alzheimer disease model mice: In consideration of an actual clinical trial method in humans, in which administration of a therapeutic agent is started after development of Alzheimer's disease, and clinical confirmed diagnosis of Alzheimer's disease, an administration method for an Alzheimer's disease model double transgenic mouse was designed. Namely, follow-up was performed for one year after the birth, and from the time point when one year passed after the birth, and the mice histopathologically developed Alzheimer's disease, 5 mg/kg of the compound A was orally administered every day to the mice of the compound A administration group by using a stomach tube. To the mice of the 0.5% methylcellulose control group, 0.5% methylcellulose alone was orally administered every day in a volume of 10 mL per 1 kg of mouse body weight (10 mL/kg) by using a stomach tube. The mice were euthanized at the time point of 730 to 745 days old after the birth after the administration of about one year, and samples of internal organ tissue were collected (sampled).

In the present invention, the alkyl group or alkyl moiety of a substituent containing an alkyl moiety (aralkyl group etc.) may be any of straight, branched, cyclic alkyl groups and an alkyl group consisting of any combination of the foregoings.

In the present invention, as the alkyl group as $L^1$ or $L^2$, alkyl group as $R^1$, alkyl group substituted with 1 to 3 halogen atoms as $R^1$, alkyl group as $R^4$, alkyl moiety of the alkylcarbonyl group as $R^4$, alkyl group as $R^5$ or $R^6$, alkyl group as $R^2$, alkyl group substituted with 1 to 3 halogen atoms as $R^2$, alkyl group as $R^3$, alkyl moiety of the alkylaminocarbonyl group as $R^3$, and alkyl group as $R^{11}$, an alkyl group having 1 to 8 carbon atoms can be used. Examples of the alkyl group or alkyl moiety having 1 to 8 carbon atoms include, for example, methyl group, ethyl group, n-propyl group, isopropyl group, n-butyl group, isobutyl group, sec-butyl group, tert-butyl group, n-pentyl group, isopentyl group, 2-methylbutyl group, 1-methylbutyl group, neopentyl group, 1,2-dimethylpropyl group, 1-ethylpropyl group, n-hexyl group, 4-methylpentyl group, 3-methylpentyl group, n-heptyl group, n-octyl group, and the like, as well as a cycloalkyl group such as cyclopropyl, cyclobutyl, cyclopentyl, and cyclohexyl, cyclopropylmethyl group, cyclopropylbutyl group, and the like, but are not limited to these.

In the present invention, as the alkenyl group as $L^1$ or $L^2$, an alkenyl group having 2 to 8 carbon atoms can be used. The alkenyl group may contain one or two or more double bonds, and when it may exist as geometric isomers, it may be an arbitrary isomer. Examples of the alkenyl group include, for example, vinyl group, prop-1-en-1-yl group, allyl group, isopropenyl group, but-1-en-1-yl group, but-2-en-1-yl group, but-3-en-1-yl group, 2-methylprop-2-en-1-yl group, 1-methylprop-2-en-1-yl group, pent-1-en-1-yl group, pent-2-en-1-yl group, pent-3-en-1-yl group, pent-4-en-1-yl group, 3-methylbut-2-en-1-yl group, 3-methylbut-3-en-1-yl group, hex-1-en-1-yl group, hex-2-en-1-yl group, hex-3-en-1-yl group, hex-4-en-1-yl group, hex-5-en-1-yl group, 2-cyclopropen-1-yl group, 2-cyclobuten-1-yl group, 2-cyclopenten-1-yl group, 3-cyclopenten-1-yl group, 2-cyclohexen-1-yl group, 3-cyclohexen-1-yl, 1-cyclobuten-1-yl group, 1-cyclopenten-1-yl group, and the like, but are not limited to these.

In the present invention, as the alkoxy group as $L^1$ or $L^2$, an alkoxy group having 1 to 8 carbon atoms can be used. Examples of the alkoxy group include, for example, methoxy group, ethoxy group, n-propoxy group, isopropoxy group, n-butoxy group, isobutoxy group, sec-butoxy group, tert-butoxy group, n-pentyloxy group, isopentyloxy group, 2-methylbutoxy group, 1-methylbutoxy group, neopentyloxy group, 1,2-dimethylpropoxy group, 1-ethylpropoxy group, n-hexyloxy group, 4-methylpentyloxy group, 3-methylpentyloxy group, 2-methylpentyloxy group, 1-methylpentyloxy group, 3,3-dimethylbutoxy group, 2,2-dimethylbutoxy group, 1,1-dimethylbutoxy group, 1,2-dimethylbutoxy group, 1,3-dimethylbutoxy group, 2,3-dimethylbutoxy group, 2-ethylbutoxy group, 1-ethylbutoxy group, 1-ethyl-1-methylpropoxy group, n-heptyloxy group, n-octyloxy, and the like, but are not limited to these.

In the present invention, as the alkyl moiety of the aralkyl group as $R^4$, alkyl moiety of the aralkylcarbonyl group as $R^4$, and alkyl moiety of the aralkyl group as $R^5$ or $R^6$, an alkyl group having 1 to 4 carbon atoms can be used. Examples of the alkyl group or alkyl moiety having 1 to 4 carbon atoms include, for example, methyl group, ethyl group, n-propyl group, isopropyl group, n-butyl group, isobutyl group, sec-butyl group, tert-butyl group, and the like, but are not limited to these.

In the present invention, as the "halogen atom", fluorine atom, chlorine atom, bromine atom, or iodine atom can be used. In the case of a group having two or more halogen atoms, they may consist of a combination of two or more kinds of halogen atoms.

Examples of the alkyl group having 1 to 8 carbon atoms and substituted with 1 to 3 halogen atoms as $R^1$ or $R^2$ include, for example, fluoromethyl group, difluoromethyl group, trifluoromethyl group, chloromethyl group, dichloromethyl group, trichloromethyl group, bromomethyl group, dibromomethyl group, tribromomethyl group, iodomethyl group, diiodomethyl group, triiodomethyl group, 2,2,2-trifluoroethyl group, 3,3,3-trifluoropropyl group, and the like, but are not limited to these.

An expression used in this specification that a certain functional group may have a specific substituent, as used for, for example, the alkyl group as $R^4$, means that the functional group is unsubstituted, or has one or two or more of the specific substituent or substituents at chemically substitutable position. Number and substituting position of substituent existing in a functional group is not particularly limited, and when two or more substituents exist, they may be the same or different.

In the present invention, the aralkyl group, or aralkyl moiety of the aralkylcarbonyl group containing an aralkyl moiety means an alkyl group having 1 to 4 carbon atoms and substituted with one or two or more aryl groups, preferably an alkyl group having 1 to 4 carbon atoms and substituted with one aryl group.

In the present invention, as the aryl group, or aryl moiety constituting the aralkyl group, arylcarbonyl group, or aralkylcarbonyl group containing an aryl moiety, a monocyclic or bicyclic aromatic hydrocarbon group having 6 to 10 carbon atoms can be used. Examples of the aryl group or aryl moiety include, for example, phenyl group, 1-naphthyl group, 2-naphthyl group, anthryl group, phenanthryl group, acenaphthylenyl group, and the like.

Examples of the aralkyl group include, for example, benzyl group, 1-naphthylmethyl group, 2-naphthylmethyl group, anthracenylmethyl group, phenanthrenylmethyl group, acenaphthylenylmethyl group, diphenylmethyl group, 1-phenethyl group, 2-phenethyl group, 1-(1-naphthyl)ethyl group, 1-(2-naphthyl)ethyl group, 2-(1-naphthyl)ethyl group, 2-(2-naphthyl)ethyl group, 3-phenylpropyl group, 3-(1-naphthyl)propyl group, 3-(2-naphthyl)propyl group, 4-phenylbutyl group, 4-(1-naphthyl)butyl group, 4-(2-naphthyl)butyl group, and the like, but are not limited to these.

In the present invention, the aryl group or the aryl moiety may have a substituent. When the aryl group has a substituent, examples of the substituent include, for example, a halogen atom, oxo group, thioxo group, nitro group, nitroso group, cyano group, isocyano group, cyanato group, thiocyanato group, isocyanato group, isothiocyanato group, hydroxy group, sulfanyl group, carboxy group, sulfanylcarbonyl group, oxalo group, mesoxalo group, thiocarboxy group, dithiocarboxy group, carbamoyl group, thiocarbamoyl group, sulfo group, sulfamoyl group, sulfino group, sulfinamoyl group, sulfeno group, sulfenamoyl group, phosphono group, hydroxyphosphonyl group, hydrocarbon group, heterocyclic group, hydrocarbon-oxy group, heterocyclyloxy group, hydrocarbon-sulfanyl group, heterocyclylsulfanyl group, an acyl group, amino group, hydrazino group, hydrazono group, diazenyl group, ureido group, thioureido group, guanidine group, carbamoimidoyl group (amidino group), azido group, imino group, hydroxyamino group, hydroxyimino group, aminoxy group, diazo group, semicarbazino group, semicarbazono group, allophanyl group, hydantoyl group, phosphano group, phosphoroso group, phospho group, boryl group, silyl group, stanyl group, selanyl group, oxido group, and the like, but are not limited to these.

In the present invention, as the heteroaryl group having 4 to 9 carbon atoms as $L^1$ or $L^2$, a monocyclic or condensed polycyclic heteroaryl group containing at least one heteroatom selected from the group consisting of oxygen atom, sulfur atom, nitrogen atom, and the like as a ring-constituting atom can be used. When two or more ring-constituting heteroatoms are contained, they may be the same or different.

Examples of the monocyclic heteroaryl group include, for example, 5- to 7-membered monocyclic heteroaryl groups such as 2-furyl group, 3-furyl group, 2-thienyl group, 3-thienyl group, 1-pyrrolyl group, 2-pyrrolyl group, 3-pyrrolyl group, 2-oxazolyl group, 4-oxazolyl group, 5-oxazolyl group, 3-isoxazolyl group, 4-isoxazolyl group, 5-isoxazolyl group, 2-thiazolyl group, 4-thiazolyl group, 5-thiazolyl group, 3-isothiazolyl group, 4-isothiazolyl group, 5-isothiazolyl group, 1-imidazolyl group, 2-imidazolyl group, 4-imidazolyl group, 5-imidazolyl group, 1-pyrazolyl group, 3-pyrazolyl group, 4-pyrazolyl group, 5-pyrazolyl group, (1,2,3-oxadiazol)-4-yl group, (1,2,3-oxadiazol)-5-yl group, (1,2,4-oxadiazol)-3-yl group, (1,2,4-oxadiazol)-5-yl group, (1,2,5-oxadiazol)-3-yl group, (1,2,5-oxadiazol)-4-yl group, (1,3,4-oxadiazol)-2-yl group, (1,3,4-oxadiazol-5-yl group, furazanyl group, (1,2,3-thiadiazol)-4-yl group, (1,2,3-thiadiazol)-5-yl group, (1,2,4-thiadiazol)-3-yl group, (1,2,4-thiadiazol)-5-yl group, (1,2,5-thiadiazol)-3-yl group, (1,2,5-thiadiazol)-4-yl group, (1,3,4-thiadiazolyl)-2-yl group, (1,3,4-thiadiazolyl)-5-yl group, (1H-1,2,3-triazol)-1-yl group, (1H-1,2,3-triazol)-4-yl group, (1H-1,2,3-triazol)-5-yl group, (2H-1,2,3-triazol)-2-yl group, (2H-1,2,3-triazol)-4-yl group, (1H-1,2,4-triazol)-1-yl group, (1H-1,2,4-triazol)-3-yl group, (1H-1,2,4-triazol)-5-yl group, (4H-1,2,4-triazol)-3-yl group, (4H-1,2,4-triazol)-4-yl group, (1H-tetrazol)-1-yl group, (1H-tetrazol)-5-yl group, (2H-tetrazol)-2-yl group, (2H-tetrazol)-5-yl group, 2-pyridyl group, 3-pyridyl group, 4-pyridyl group, 3-pyridazinyl group, 4-pyridazinyl group, 2-pyrimidinyl group, 4-pyrimidinyl group, 5-pyrimidinyl group, 2-pyrazinyl group, (1,2,3-triazin)-4-yl group, (1,2,3-triazin)-5-yl group, (1,2,4-triazin)-3-yl group, (1,2,4-triazin)-5-yl group, (1,2,4-triazin)-6-yl group, (1,3,5-triazin)-2-yl group, 1-azepinyl group, 2-azepinyl group, 3-azepinyl group, 4-azepinyl group, (1,4-oxazepin)-2-yl group, (1,4-oxazepin)-3-yl group, (1,4-oxazepin)-5-yl group, (1,4-oxazepin)-6-yl group, (1,4-oxazepin)-7-yl group, (1,4-thiazepin)-2-yl group, (1,4-thiazepin)-3-yl group, (1,4-thiazepin)-5-yl group, (1,4-thiazepin)-6-yl group, and (1,4-thiazepin)-7-yl group, but are not limited to these.

Examples of the condensed polycyclic heteroaryl group include, for example, 8- to 14-membered condensed polycyclic heteroaryl groups such as 2-benzofuranyl group, 3-benzofuranyl group, 4-benzofuranyl group, 5-benzofuranyl group, 6-benzofuranyl group, 7-benzofuranyl group, 1-isobenzofuranyl group, 4-isobenzofuranyl group, 5-isobenzofuranyl group, 2-benzo[b]thienyl group, 3-benzo[b]thienyl group, 4-benzo[b]thienyl group, 5-benzo[b]thienyl group, 6-benzo[b]thienyl group, 7-benzo[b]thienyl group, 1-benzo[c]thienyl group, 4-benzo[c]thienyl group, 5-benzo[c]thienyl group, 1-indolyl group, 2-indolyl group, 3-indolyl group, 4-indolyl group, 5-indolyl group, 6-indolyl group, 7-indolyl group, (2H-isoindol)-1-yl group, (2H-isoindol)-2-yl group, (2H-isoindol)-4-yl group, (2H-isoindol)-5-yl group, (1H-indazol)-1-yl group, (1H-indazol)-3-yl group, (1H-indazol)-4-yl group, (1H-indazol)-5-yl group, (1H-indazol)-6-yl group, (1H-indazol)-7-yl group, (2H-indazol)-1-yl group, (2H-indazol)-2-yl group, (2H-indazol)-4-yl group, (2H-indazol)-5-yl group, 2-benzoxazolyl group, 2-benzoxazolyl group, 4-benzoxazolyl group, 5-benzoxazolyl group, 6-benzoxazolyl group, 7-benzoxazolyl group, (1,2-benzoisoxazol)-3-yl group, (1,2-benzoisoxazol)-4-yl group, (1,2-benzoisoxazol)-5-yl group, (1,2-benzoisoxazol)-6-yl group, (1,2-benzoisoxazol)-7-yl group, (2,1-benzoisoxazol)-3-yl group, (2,1-benzoisoxazol)-4-yl group, (2,1-benzoisoxazol)-5-yl group, (2, 1-benzoisoxazol)-6-yl group, (2, 1-benzoisoxazol)-7-yl group, 2-benzothiazolyl group, 4-benzothiazolyl group, 5-benzothiazolyl group, 6-benzothiazolyl group, 7-benzothiazolyl group, (1,2-benzoisothiazol)-3-yl group, (1,2-benzoisothiazol)-4-yl group, (1,2-benzoisothiazol)-5-yl group, (1,2-benzoisothiazol)-6-yl group, (1,2-benzoisothiazol)-7-yl group, (2, 1-benzoisothiazol)-3-yl group, (2,1-benzoisothiazol)-4-yl group, (2, 1-benzoisothiazol)-5-yl group, (2, 1-benzoisothiazol)-6-yl group, (2,1-benzoisothiazol)-7-yl group, (1,2,3-benzoxadiazol)-4-yl group, (1,2,3-benzoxadiazol)-5-yl group, (1,2,3-benzoxadiazol)-6-yl group, (1,2,3-benzoxadiazol)-7-yl group, (2, 1,3-benzoxadiazol)-4-yl group, (2, 1,3-benzoxadiazol)-5-yl group, (1,2,3-benzothiadiazol)-4-yl group, (1,2,3-benzothiadiazol)-5-yl group, (1,2,3-benzothiadiazol)-6-yl group, (1,2,3-benzothiadiazol)-7-yl group, (2, 1,3-benzothiadiazol)-4-yl group, (2,1,3-benzothiadiazol)-5-yl group, (1H-benzotriazol)-1-yl group, (1H-benzotriazol)-4-yl group, (1H-benzotriazol)-5-yl group, (1H-benzotriazol)-6-yl group, (1H-benzotriazol)-7-yl group, (2H-benzotriazol)-2-yl group, (2H-benzotriazol)-4-yl group, (2H-benzotriazol)-5-yl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 3-cinnolinyl group, 4-cinnolinyl group, 5-cinnolinyl group, 6-cinnolinyl group, 7-cinnolinyl group, 8-cinnolinyl group, 2-quinazolinyl group, 4-quinazolinyl group, 5-quinazolinyl group, 6-quinazolinyl group, 7-quinazolinyl group, 8-quinazolinyl group, 2-quinoxalinyl group, 5-quinoxalinyl group, 6-quinoxalinyl group, 1-phthalazinyl group, 5-phthalazinyl group, 6-phthalazinyl group, 2-naphthyridinyl group, 3-naphthyridinyl group, 4-naphthyridinyl group, 2-purinyl group, 6-purinyl group, 7-purinyl group, 8-purinyl group, 2-pteridinyl group, 4-pteridinyl group, 6-pteridinyl group, 7-pteridinyl group, 1-carbazolyl group, 2-carbazolyl group, 3-carbazolyl group, 4-carbazolyl group, 9-carbazolyl group, 2-(α-carbolinyl) group, 3-(α-carbolinyl) group, 4-(α-carbolinyl) group, 5-(α-carbolinyl) group, 6-(α-carbolinyl) group, 7-(α-carbolinyl) group, 8-(α-carbolinyl) group, 9-(α-carbolinyl) group, 1-(β-carbolinyl) group, 3-(β-carbolinyl) group, 4-(β-carbolinyl) group, 5-(β-carbolinyl) group, 6-(β-carbolinyl) group, 7-(β-carbolinyl) group, 8-(β-carbolinyl) group, 9-(β-carbolinyl) group, 1-(γ-carbolinyl) group, 2-(γ-carbolinyl) group, 4-(γ-carbolinyl) group, 5-(γ-carbolinyl) group, 6-(γ-carbolinyl) group, 7-(γ-carbolinyl) group, 8-(γ-carbolinyl) group, 9-(γ-carbolinyl) group, 1-acridinyl group, 2-acridinyl group, 3-acridinyl group, 4-acridinyl group, 9-acridinyl group, 1-phenoxazinyl group, 2-phenoxazinyl group, 3-phenoxazinyl group, 4-phenoxazinyl group, 10-phenoxazinyl group, 1-phenothiazinyl group, 2-phenothiazinyl group, 3-phenothiazinyl group, 4-phenothiazinyl group, 10-phenothiazinyl group, 1-phenazinyl group, 2-phenazinyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 2-phenanthrolinyl group, 3-phenanthrolinyl group, 4-phenanthrolinyl group, 5-phenanthrolinyl group, 6-phenanthrolinyl group, 7-phenanthrolinyl group, 8-phenanthrolinyl group, 9-phenanthrolinyl group, 10-phenanthrolinyl group, 1-thianthrenyl group, 2-thianthrenyl group, 1-indolizinyl group, 2-indolizinyl group, 3-indolizinyl group, 5-indolizinyl group, 6-indolizinyl group, 7-indolizinyl group, 8-indolizinyl group, 1-phenoxathiinyl group, 2-phenoxathiinyl group, 3-phenoxathiinyl group, 4-phenoxathiinyl group, thieno[2,3-b]furyl group, pyrrolo[1,2-b]pyridazinyl group, pyrazolo[1,5-a]pyridyl group, imidazo[11,2-a]pyridyl group, imidazo[1,5-a]pyridyl group, imidazo[1,2-b]pyridazinyl group, imidazo[1,2-a]pyrimidinyl group, 1,2,4-triazolo[4,3-a]pyridyl group, and 1,2,4-triazolo[4,3-a]pyridazinyl group, but are not limited to these.

As for the aforementioned general formula (A), when $Z^1$ is carbon atom, it is preferred that $R^1$ is $OR^4$. In this case, it is more preferred that $R^4$ is an alkyl group having 1 to 8 carbon atoms, which may have a substituent selected from the group consisting of a halogen atom, hydroxy group, nitro group, and cyano group, or $R^4$ is an aryl group having 6 to 10 carbon atoms. It is further preferred that $R^1$ is an alkoxy group of 1 to 5 carbon atoms, which may have a substituent selected from the group consisting of a halogen atom, hydroxy group, nitro group, and cyano group, or $R^1$ is phenoxy group. When $L^1$ and $L^2$ combine together to form a bicyclic heteroaryl ring, it is preferred that $R^1$ is methoxy group or phenoxy group. When $L^1$ and $L^2$ do not combine together, it is preferred that $R^1$ is an alkoxy group having 1 to 5 carbon atoms, and it is particularly preferred that $R^1$ is isobutoxy group.

As for the aforementioned general formula (A), it is preferred that $R^2$ is a halogen atom, nitro group, cyano group, or $CO_2R^7$, and it is more preferred that $R^2$ is a halogen atom, nitro group, cyano group, or carboxyl group. It is particularly preferred that $R^2$ is cyano group.

As for the aforementioned general formula (A), it is preferred that $Z^2$ is carbon atom. In this case, it is preferred that $L^1$ is an alkyl group having 1 to 8 carbon atoms, or a heteroaryl group having 4 to 9 carbon atoms, and it is more preferred that $L^1$ is methyl group, or 4-pyridyl group.

As for the aforementioned general formula (A), it is preferred that X is sulfur atom, or nitrogen atom. When X is sulfur atom, it is preferred that $Z^8$ is carbon atom, and $L^2$ is carboxyl group, and when X is nitrogen atom, it is preferred that $Z^3$ is —NH—.

As for the aforementioned general formula (A), when $Z^2$ and $Z^3$ are carbon atoms, it is preferred that $L^1$ and $L^2$ combine together to form a bicyclic heteroaryl ring together with the 5-membered ring to which they bond. It is preferred that the ring formed by $L^1$ and $L^2$ that combine together (except for the 5-membered ring to which they bond) is a 6-membered ring, and it is more preferred that it contains one or two heteroatoms. It is further preferred that the ring contains two nitrogen atoms, and it is particularly preferred that the bicyclic heteroaryl ring defined for the aforementioned general formula (I) is formed.

As for the aforementioned general formula (I), it is preferred that $R^1$ is $OR^4$. In this case, it is more preferred that $R^4$ is an alkyl group having 1 to 8 carbon atoms, which may have a substituent selected from the group consisting of a halogen atom, hydroxy group, nitro group, and cyano group, or $R^4$ is an aryl group having 6 to 10 carbon atoms. It is further preferred that $R^1$ is an alkoxy group having 1 to 5 carbon atoms, which may have a substituent selected from the group consisting of a halogen atom, hydroxy group, nitro group, and cyano group, or $R^1$ is phenoxy group.

As for the aforementioned general formula (I), it is preferred that $R^2$ is a halogen atom, nitro group, cyano group, or $CO_2R^7$, and it is more preferred that $R^2$ is a halogen atom, nitro group, cyano group, or carboxyl group. It is particularly preferred that $R^2$ is cyano group.

As for the aforementioned general formula (I), it is preferred that $R^3$ is hydrogen atom, amino group, hydroxy group, a halogen atom, or $CO_2R^8$, and it is more preferred that $R^3$ is hydrogen atom, amino group, hydroxy group, a halogen atom, or carboxyl group.

As for the aforementioned general formula (I), it is preferred that X is oxygen atom, or sulfur atom. In the aforementioned general formula (I), it is preferred that both Y and Z are nitrogen atoms.

As for the aforementioned general formula (I), it is particularly preferred that $R^1$ is an alkoxy group having 1 to 5 carbon atoms, or phenoxy group, which may have a substituent selected from the group consisting of a halogen atom, hydroxy group, nitro group, and cyano group, $R^2$ is nitro group, cyano group, a halogen atom, or carboxyl group, $R^9$ is hydrogen atom, amino group, hydroxy group, a halogen atom, or carboxyl group, X is oxygen atom, or sulfur atom, and both Y and Z are nitrogen atoms, and it is most preferred that $R^1$ is an alkoxy group having 1 to 5 carbon atoms or phenoxy group, $R^2$ is cyano group, $R^3$ is hydroxy group, and X is oxygen atom, or sulfur atom, and both Y and Z are nitrogen atoms.

As the active ingredient of the medicament of the present invention, besides a compound represented by the general formula (A) or general formula (I) in free form, such a compound in the form of a salt may be used. Type of the salt is not particularly limited, and an arbitrary salt can be used so long as it is a physiologically acceptable salt. Example of the salt include, for example, alkali metal salts such as salts with sodium, potassium, etc.; alkaline earth metal salts such as salts with calcium, magnesium etc.; organic amine salts such as salts with methylamine, ethylamine, diethanolamine, etc.; mineral acid salts such as hydrochlorides, sulfates, and nitrates, organic acid salts such as p-toluenesulfonates, maleates, and tartrates, and the like, but are not limited to these.

As the active ingredient of the medicament of the present invention, an arbitrary solvate of a compound represented by the general formula (A) or general formula (I), or a salt thereof may be used. Type of the solvent constituting the solvate is not particularly limited, and examples include, for example, water (namely, hydrate), ethanol, ethyl acetate, acetone, and the like. The compounds represented by the general formula (A) or general formula (I) may exist as an isomer such as optical isomer, diastereoisomer, or tautomer depending on type of substituent. An arbitrary isomer in pure form as well as a mixture of arbitrary isomers can be used as the active ingredient of the medicament of the present invention. As the active ingredient of the medicament of the present invention, a crystalline substance in an arbitrary form, amorphous substance in an arbitrary form, an arbitrary mixture of a crystalline substance and an amorphous substance, and the like can be used.

Although the method for obtaining the compounds represented by the general formula (A) or general formula (I) is not particularly limited, they can be synthesized from easily obtainable starting compounds according to the methods described in, for example, International Patent Publications WO2003/42185, WO2005/121153, WO2007/4688, Japanese Patent Nos. 3600832, 3779725, Japanese Patent Unexamined Publication (KOKAI) No. 2005-41802, Japanese Patent Nos. 2725886, 2706037, 3202607, and the like. All the disclosures of the aforementioned patent documents are incorporated into the disclosure of the present specification by reference.

The medicament of the present invention can be used as a medicament for prophylactic and/or therapeutic treatment of dementia. In the present invention, the prophylactic and/or therapeutic treatment of dementia includes preventing advance of dementia already developed. Examples of the dementia as object of the application of the medicament of the present invention include, for example, Alzheimer type dementia.

The medicament of the present invention can also be applied to dementia selected from the group consisting of senile dementia, mild cognitive disorder, mild dysgnosia, age-associated memory impairment (AAMI), senile dementia, AIDS dementia, Pick's disease, Down's syndrome-related dementia, cerebrovascular dementia, senile memory disorder, learning disorder, hippocampal degeneration, cognitive dysfunction, and microinfarct dementia. However, the object of the application of the medicament of the present invention is not limited to these, and it can also be applied to a patient in an early stage of dementia or before development of dementia, who is diagnosed to be suspected to have dementia or to have a possibility of developing dementia by a skillful medical practitioner.

The medicament of the present invention is generally provided in the form of a pharmaceutical composition utilizing one or two or more kinds of pharmaceutical additives commonly used in this field. For example, it can be provided in the form of a pharmaceutical composition for oral administration such as capsule, tablet, syrup, powder, granule, subtilized granule, or solution, injection or fusion drip for intravenous administration, injection for intramuscular administration or subcutaneous administration, inhalant, percutaneous absorption preparation, or the like, but the form of the medicament is not limited to these forms. The medicament of the present invention can be formed by the methods well known to those skilled in the art with appropriately choosing pharmaceutical additives depending on the form of the pharmaceutical composition.

Method for administration and time of administration of the medicament of the present invention are not particularly limited, and they can be appropriately chosen depending on the purpose such as prophylactic or therapeutic purpose, severity of dementia, and the like. Dose of the medicament of the present invention can be appropriately chosen in consideration of various factors such as age, body weight, body constitution, and symptoms of patients, as well as whether medicaments containing other ingredients as active ingredients are administered or not.

EXAMPLES

Hereafter, the present invention will be still more specifically explained with reference to examples. However, the scope of the present invention is not limited by the following examples.

Example 1

(a) Materials and Methods

As a compound having an action for potently inhibiting xanthine oxioreductase, 5-(7-hydroxythiazolo[5,4-d]pyrimidin-2-yl)-2-phenoxy-benzonitrile (2-(3-cyano-4-phenoxyphenyl)-4-hydroxythiazolo[5,4-d]pyrimidine, which is the compound described in Japanese Patent No. 4914210, claim 1, henceforth referred to as compound A), was used.

Concentration of the compound A was adjusted as follows, and dose and administration method of the compound A were as follows.

As a base, 0.5% methylcellulose was prepared. When the compound A was dissolved in 0.5% methylcellulose as the solvent for the preparation of an agent for administering the compound A, a stock solution of the compound A having 10-fold concentration was once prepared in order to avoid weighing error of the medicament used in an extremely small amount and degradation of efficacy. That is, the compound A was mashed in an agate mortar, a small volume of 0.5% methylcelluloses was added to suspend the compound, and then 0.5% methylcelluloses was gradually added portionwise in small volumes to completely suspend and dissolve the compound. The compound A in an amount of 50 mg was finally suspended and dissolved in 10 mL of 0.5% methylcellulose to prepare a stock solution of 10-fold concentration of 50 mg of the compound A and 10 mL of 0.5% methylcellulose (50 mg/10 mL). The stock solution having 10-fold concentration [50 mg of compound A and 10 mL of 0.5% methylcellulose (50 mg/10 mL)] was prepared every week and refrigerated. On each day of administration, the stock solution of 10-fold concentration was diluted 10 times with full stirring, and also at the time of administration to mice, the stirred solution was sucked into a stomach tube to obtain a concentration for administration.

As described above, a test solution having such a concentration that 5 mg of the compound A is suspended and dissolved in 10 mL of 0.5% methylcellulose, i.e., 5 mg compound A in 10 mL of 0.5% methylcellulose (5 mg/10 mL), as the administration concentration, was finally prepared, and 5 mg of the compound A per 1 kg of mouse body weight (5 mg/kg) was orally administered once a day.

As a placebo, 10 mL per 1 kg of mouse body weight of 0.5% methylcellulose as the solvent (10 mL/kg) alone, i.e., the solvent of the same volume as the volume of the solvent administered to the medicament administration mice, was orally administered once a day.

As for the method of the oral administration, the volume was correctly measured in a plastic syringe, a stomach tube for mice was directly connected to the plastic syringe, and the medicament was surely orally administered through the esophagus.

As animals for experiments, Tg(APPSWE)2576KhaTg (Prnp-MAPT*P301L)JNPL3HImc Alzheimer's disease model double transgenic mice that highly express both of the human gene encoding 695 amino acids of the amyloid β (Aβ) precursor protein of human Alzheimer's disease and having a Sweden mutation, and the human tau protein gene having a mutation for substitution of leucine for proline at the position 301 (P301L) were used (purchased from Taconic Farms, Inc., Hudson, N.Y., U.S.A.). These Alzheimer's disease model double transgenic mice were bred under SPF (specific pathogen free, microorganism-controlled state free from specific pathogens) conditions, and they are viable for about two years.

Because the experiment was performed over a long period of time, after the Alzheimer's disease model double transgenic mice were purchased, they were individually isolated over four weeks to confirm again that they were SPF, in order to eliminate infectious diseases, and the like in the mice harboring naturally colonized microorganisms, and minimize individual differences as much as possible. Ten male mice were divided into two groups each consisting 5 mice, the compound A treatment and administration group (n=5) and methylcellulose administration group as a control group (n=5).

Emergence of senile plaques and neurofibrillary tangles as hallmarks of histopathological images of human Alzheimer's disease is confirmed in the cerebrums of these mice of one year old (365 days old) or older as a natural process, whereas senile plaques and neurofibrillary tangles are not observed in the cerebrums of 2 years old normal mice. On the basis of this finding and the neuropathological findings of human Alzheimer's disease, it was concluded that the one year old mice developed a disease equivalent to Alzheimer's disease in human. On the basis of this conclusion, and also in consideration of actual clinical application to humans, the administration was started at the time point of one year after the birth when senile plaques and neurofibrillary tangles as the hallmarks of pathological tissue images of Alzheimer's disease appear (after development of Alzheimer's disease).

The mice were followed up until the time point of one year after the birth, and from the time point of one year after the birth, 5 mg/kg of the compound A was orally administered every day to the mice of the compound A treatment group (n=5) by using a stomach tube. To the mice of the 0.5% methylcellulose control group (n=5), 10 mL per 1 kg body weight of mouse (10 mL/kg) of 0.5% methylcellulose alone was orally administered every day by using a stomach tube (FIG. 1).

Since one mouse suddenly died in each of the compound A treatment group and the 0.5% methylcellulose control group before the 700th day after the birth, 4 animals that survived 700 days or longer after the birth in the compound A treatment group and 4 animals that similarly survived in the 0.5% methylcellulose control group, 8 animals in total, were adopted as experimental animals.

At the time point of 730 to 745 days old after the birth, internal organ tissues of the individuals of the 4 animals of the compound A treatment group and 4 animals of the 0.5% methylcellulose control group, 8 animals in total, were sampled as follows.

The 8 mice were systemically anesthetized by intraperitoneally injecting pentobarbital sodium (trade name, Nembutal; Dainippon Sumitomo Pharma) in a volume of 1 mL per 1 g of individual body weight. After confirming that the animals were completely under anesthesia, the individuals were euthanized by a carbon dioxide treatment, and laparotomy and thoracotomy were performed. After blood was collected from the right ventricle, the blood of internal organs of the whole body was removed with physiological saline injected via the aorta of the left ventricle. Then, fresh internal organs of a part of the right frontal lobe of the cerebrum, a part of the spine, parts of both the right and left ventricles of the heart, a part of the right lung, a part of the liver, parts of the right and left kidneys, and the left testis were immediately extracted, and they were instantly frozen with dry ice. Then, the fresh internal organs and serum were stored in an ultra-deep freezer at −80° C. At the same time as the instantaneous freezing operation, remained parts of the organs other than the parts collected as the fresh internal organs and all the other organs were immediately fixed by infiltration of 4% paraformaldehyde and 0.1 M cacodylate buffer (pH 7.3).

All the internal organs including the cerebrum, cerebellum, brain stem, spine, and the like were embedded in paraffin, and sectioned with a microtome. The organ tissues were treated by the following six steps of fixation of the internal organ tissues, dehydration, de-ethanolation, paraffin impregnation, parafin embedding, and paraffin section preparation.

1) Fixation of the internal organ tissues was performed by infiltration fixation with 4% paraformaldehyde and 0.1 M cacodylate buffer (pH 7.3).

2) Dehydration of the internal organ tissues was performed as follows. Namely, the tissues were washed 3 times with phosphate buffered saline (PBS). Then, the tissues were washed overnight with running water of water supply, and then impregnated with 70% ethanol for 12 hours at room temperature, 80% ethanol for 12 hours at room temperature, 90% ethanol for 12 hours at room temperature, 99.5% ethanol for 12 hours at room temperature, again 99.5% ethanol for 12 hours at room temperature, 100% ethanol for 12 hours at room temperature, and anhydrous ethanol for 12 hours at room temperature to completely replace the moisture of the internal organ tissues with ethanol.

3) In order to remove the ethanol for dehydration, it was replaced with chloroform. For the replacement with chloroform, tissues were impregnated with chloroform 3 times over 2 hours for each time at room temperature in a chloroform bath.

4) The step of paraffin impregnation of the internal organ tissues was carried out by transferring the internal organ tissues from the chloroform bath to a 60° C. paraffin bath.

5) Chloroform was completely removed by impregnation performed 4 times over 2 hours for each time in the 60° C. paraffin bath, and the internal organ tissues were completely impregnated with paraffin. Then, the internal organ tissues were embedded in paraffin by using paraffin for embedment.

6) Paraffin sections were prepared by sectioning the paraffin blocks of the paraffin-embedded internal organ tissues in a thickness of 6 μm with a microtome.

Cerebrum paraffin blocks of 4 autopsy cases of Alzheimer's disease, to which clinical neuropathological confirmed diagnoses was given, were used for the purpose of evaluating validity of the neuropathological tissue images of the cerebrums of the mice, especially the neuropathological tissue images of senile plaques and neurofibrillary tangles.

The cerebrum of each mouse was observed from the bottom, and the mammillary body was confirmed. A carbon steel double-edged razor (FA-10, Feather Safety Razor, Osaka) was broken at the center, and thereby made into two of single-edged razors. By using the single-edged razor obtained as described above, the first coronal cut surface was made at the center of the mammillary body of the cerebrum of the Alzheimer's disease model double transgenic mouse.

Starting from this coronal cut surface of the mammillary body, cerebrum coronal cut surfaces were successively formed for both the rostral direction and the caudal direction with intervals of about 2 mm. For the parts of the brain stem and cerebellum, the first cut surface was produced in a cut surface plane including the trigeminal nerves on the right and left sides of the pons cerebelli and perpendicular to the major axis of the brain stem. In the same manner as that used for the cerebrum, brain stem and cerebellum cut surfaces were successively formed for both the rostral direction and the caudal direction with intervals of about 2 mm.

Histochemical staining and immunohistochemical staining were performed by the following methods.

1) In advance of the histochemical and immunohistochemical stainings of the paraffin sections, the following deparaffinization and hydrophilization treatments were performed. The paraffin sections were immersed in a xylene bath 4 times for 5 minutes for each time as the deparaffinization treatment, and then the deparaffinized sections were immersed in a 100% ethanol bath 2 times for 5 minutes for each time, 95% ethanol bath once for 5 minutes, 90% ethanol bath once for 5 minutes, and 80% ethanol bath once for 5 minutes as the hydrophilization treatment. Then, the sections were washed for 5 minutes with running water of water supply.

2) As the histochemical staining, hematoxylin and eosin (HE) staining was performed. The HE-stained sections were subjected to the steps of dehydration, clarification, and mounting. First, the dehydration step was performed by the following procedure. The HE-stained sections were immersed in 50% ethanol once for 1 minute, 70% ethanol once for 1 minute, 80% ethanol once for 1 minute, 90% ethanol once for 1 minute, 95% ethanol once for 1 minute, 100% ethanol once for 5 minutes, and anhydrous ethanol once for 5 minutes. The clarification step was performed by 4 times of impregnation with xylene for 5 minutes for each time. The mounting step was performed by dropping a small volume of a mounting medium (New M•X, Matsunami Glass Industry, Osaka) onto cover glass, and covering the tissue section with the cover glass so as not to enclose air.

3) As for the immunohistochemical staining, detection of the amyloid β protein as the core protein of senile plaque, and detection of the phosphorylated tau protein as the core protein of neurofibrillary tangle were performed by the following methods.

(1) Method for Detecting Amyloid β Protein

An amyloid β protein immunohistochemical staining kit (Code No. 299-56701, Wako Pure Chemical Industries, Osaka) was used. For detection of Aβ40 in a paraffin section, the anti-amyloid β protein (1-40) mouse monoclonal antibody (clone No. BA27) included in the kit was used. For detection of Aβ42, the anti-amyloid β-protein (1-42) mouse monoclonal antibody (clone No. BC05) included in the kit was used. The proteins were finally visualized by using 3,3'-diaminobenzidine tetrahydrochloride (DAB, Dako, Glostrup, Denmark) as a color developer.

(2) Method for Detecting Phosphorylated Tau Protein

Detection was performed with a combination of the following primary antibody and the ABC (avidin-biotin-immunoperoxidase complex) method.

As the primary antibody, an anti-phosphorylated tau protein (PHF-tau) mouse monoclonal antibody (clone AT8, Innogenetics, presently Fujirebio, Tokyo) was used. As the ABC Kit, Vectastain ABC kit (Vector Laboratories, Burlingame, Calif., U.S.A.) was used.

Finally, visualization was performed by using DAB as a color developer. In the mounting step, the tissues section was enclosed with the mounting medium as performed in HE staining.

After drying the mounting medium, samples of the HE staining, Aβ40 immunostaining, Aβ42 immunostaining, and AT8 immunostaining were observed with a light microscope (BX41, Olympus, Tokyo) carrying a 3-CCD digital camera system (FX380, Olympus) loading image analysis software (FLVFS-LS Ver.1.12, Olympus), and image capturing and image analysis were performed with the apparatus.

Figure 2:
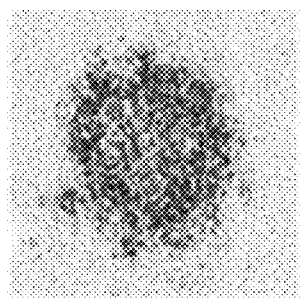
FIG. 2 Photographs showing pathological tissue images of the central nervous system with Alzheimer disease: The images on the left side show pathological symptoms of human Alzheimer's disease, and the images on the right side show pathological symptoms of an Alzheimer's disease model double transgenic mouse. Nerve cells, in which senile plaques and neurofibrillary tangles as neurohistopathological hallmarks of human Alzheimer's disease were induced, and which had senile plaques and neurofibrillary tangles as neuropathologically completely the same structures as those of humans, are also observed in the Alzheimer's disease model double transgenic mouse (images on the right side). The senile plaques were detected with anti-amyloid β-protein (1-40) mouse monoclonal antibody (clone No. BA27) and the anti-amyloid β-protein (1-42) mouse monoclonal antibody (clone No. BC05). The neurofibrillary tangles were detected with anti-phosphorylated tau protein (PHF-tau) mouse monoclonal antibody (clone AT8).
Figure 2:
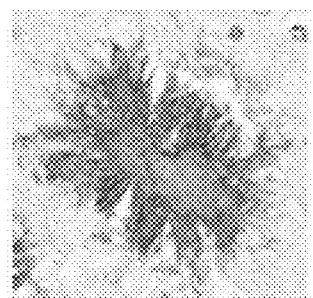
Figure 2:
Figure 2:
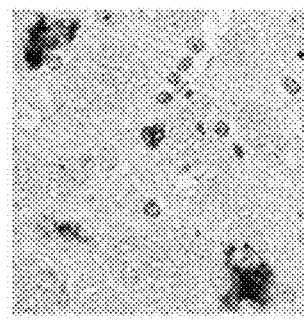

In order to verify that the pathological symptoms of the Alzheimer's disease model double transgenic mouse are neuropathologically the same as those of human Alzheimer's disease, 10 male mice were used as a preliminary experiment. By immunohistochemical analysis, it was found that many amyloid senile plaques of which core proteins are Aβ40 and Aβ42, and neurofibrillary tangles of which core protein is the phosphorylated tau protein as neuropathological diagnostic hallmarks of human Alzheimer's disease appeared in the Alzheimer's disease model double transgenic mice of 700 or more days old, but they were not observed in age-matched normal mice. The structures of the senile plaques of the Alzheimer's disease model double transgenic mice could be easily identified only by HE staining, which is routine staining, like the senile plaques of human Alzheimer's disease. The senile plaques and neurofibrillary tangles that appear in the Alzheimer's disease model double transgenic mice, and the senile plaques and neurofibrillary tangles as neurohistopathological hallmarks of human Alzheimer's disease were neuropathologically the same structures (FIG. 2).

Figure 3:
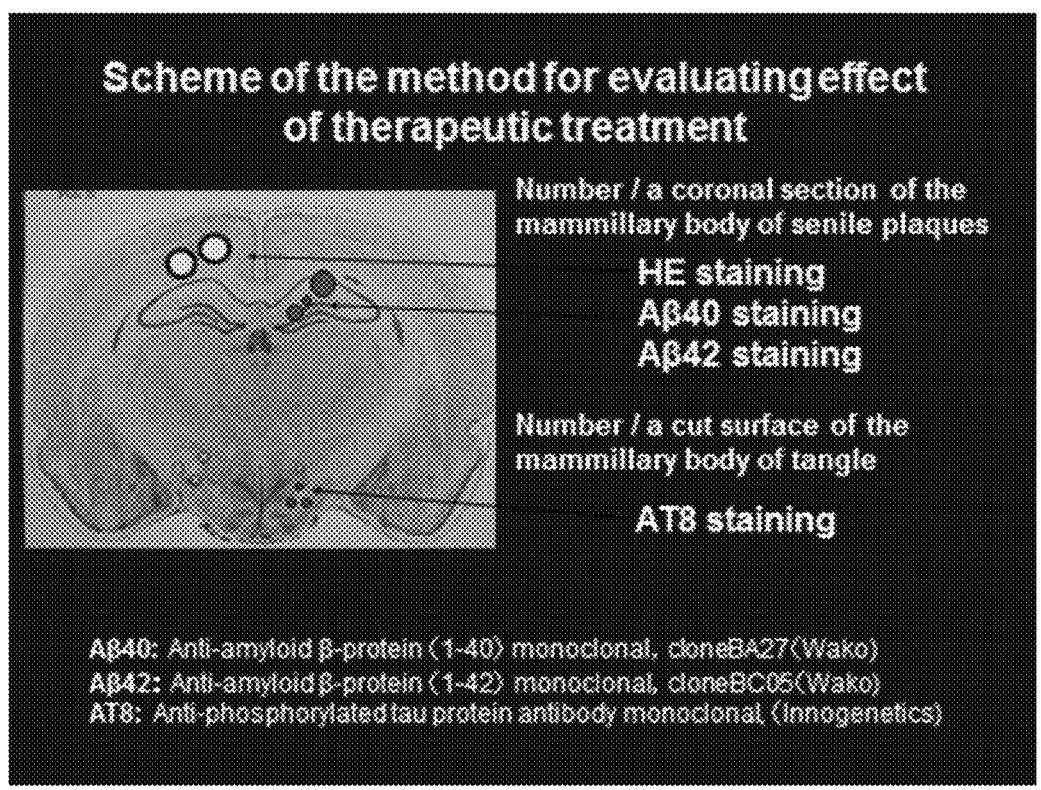
FIG. 3 Diagram showing scheme of the method for evaluating effect of therapeutic treatment with medicament: On a cut surface of the cerebrum of the Alzheimer's disease model double transgenic mouse, number of senile plaques was evaluated by HE staining, and in addition, immunohistochemical staining of the amyloid β proteins Aβ40 and Aβ42. Number of nerve cells causing neurofibrillary tangles was evaluated by immunohistochemical staining of AT8 (phosphorylated tau protein).

In the Alzheimer's disease model double transgenic mice, the favorite sites of the amyloid senile plaques, of which core proteins are Aβ40 and Aβ42, identified by immunostaining, and the senile plaques identified by HE staining were the hippocampus (Ammon angle), subiculum, and cerebral cortex (especially entorhinal cortex). The favorite sites of the neurofibrillary tangles, of which core protein is the phosphorylated tau protein, were the hypothalamus and amygdaloid nucleus. On the basis of the results of this neuropathological analysis preliminary experiment, the cerebrum cut surfaces, and brain stem and cerebellum cut surfaces of the Alzheimer's disease model double transgenic mice, mainly the cut surfaces of the favorite sites of the senile plaques and neurofibrillary tangles as neurohistopathological hallmarks of human Alzheimer's disease, were histochemically and immunohistochemically quantitatively analyzed as evaluation method for effect of drug therapy (FIG. 3).

Therapeutic effect of a medicament for Alzheimer's disease was determined by quantitatively analyzing number of senile plaques that appeared as a neurohistopathological hallmark of human Alzheimer's disease and suppression of number of nerve cells having neurofibrillary tangles as a neurohistopathological hallmark of human Alzheimer's disease in the mice according to the following methods.

Figure 4:
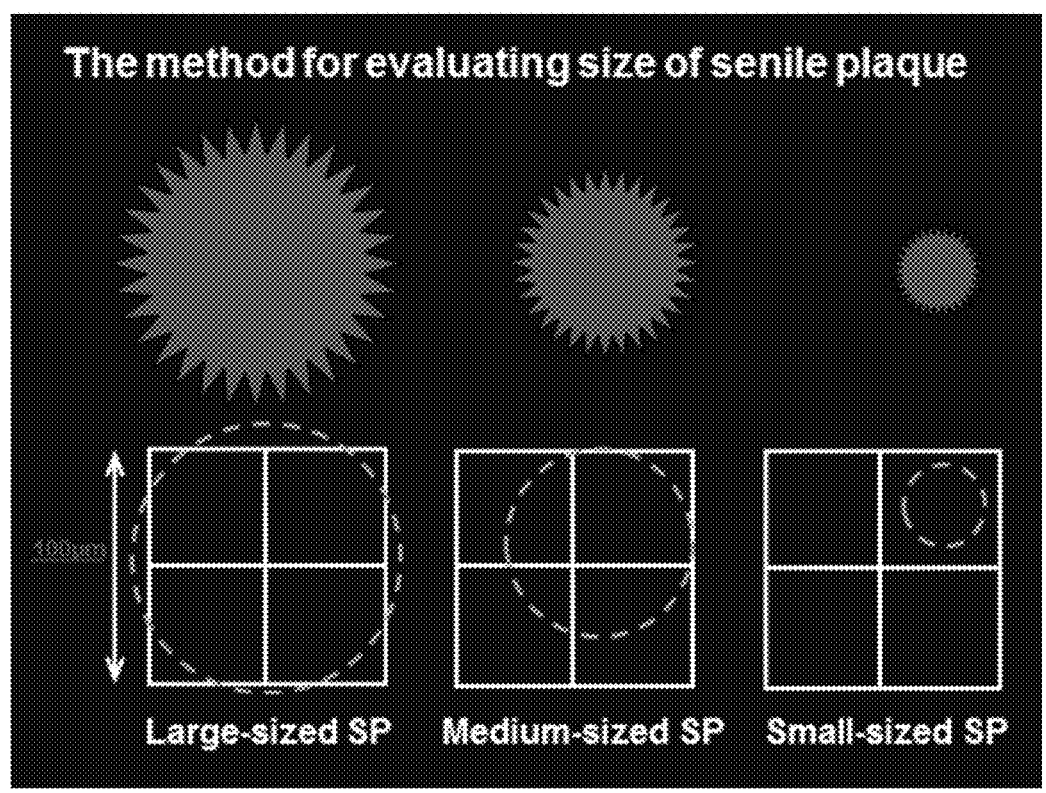
FIG. 4 Diagram showing the method for evaluating size of senile plaque: In human Alzheimer's disease, many senile plaques appear with advance of Alzheimer's disease, and the senile plaques grow with advance of Alzheimer's disease. Therefore, search was performed in consideration of two factors, i.e., number of senile plaques and size of senile plaque (growth degree of senile plaque). As the evaluation method of size of senile plaque, senile plaques having a diameter of 100 µm or larger were classified as large-sized senile plaques (large-sized SPs), those having a diameter of 50 µm or smaller as small-sized senile plaques (small-sized SPs), and those having a diameter between 50 µm and 100 µm as medium-sized senile plaques (medium SPs), and numbers of the senile plaques of respective sizes were counted.

The senile plaques were searched for in consideration of two factors, number of senile plaques and size of senile plaques (growth degree of senile plaques). That is, senile plaques having a diameter of 100 m or larger were classified as large-sized senile plaques, those having a diameter of 50 μm or smaller as small-sized senile plaques, and those having a diameter between 50 μm and 100 μm as medium-sized senile plaques, and numbers of each type of plaques were counted (FIG. 4). The count of the numbers was performed by the double blind method. That is, in the quantitative neuropathological analysis, only the individual identification numbers were attached to the samples, and the number of cells in the samples were counted in a state that it could not be known whether the samples were those of the placebo group or the compound A administration group.

The neurofibrillary tangles were evaluated only with the number of nerve cells having neurofibrillary tangles. The number was counted by the double blind method as in the count of the number of senile plaques.

The quantitative values of the number of the senile plaques that appeared and the number of nerve cells accompanied by neurofibrillary tangles are indicated as average value±standard deviation. In this examination, statistical analysis was performed by using the Macintosh software, Statview (Ver.5.0, SAS Institute Inc., California, U.S.A.). The statistical significance test was performed by using the Mann-Whitney U test, and when $P<0.05$, it was judged that there was statically significant difference.

Figure 5:
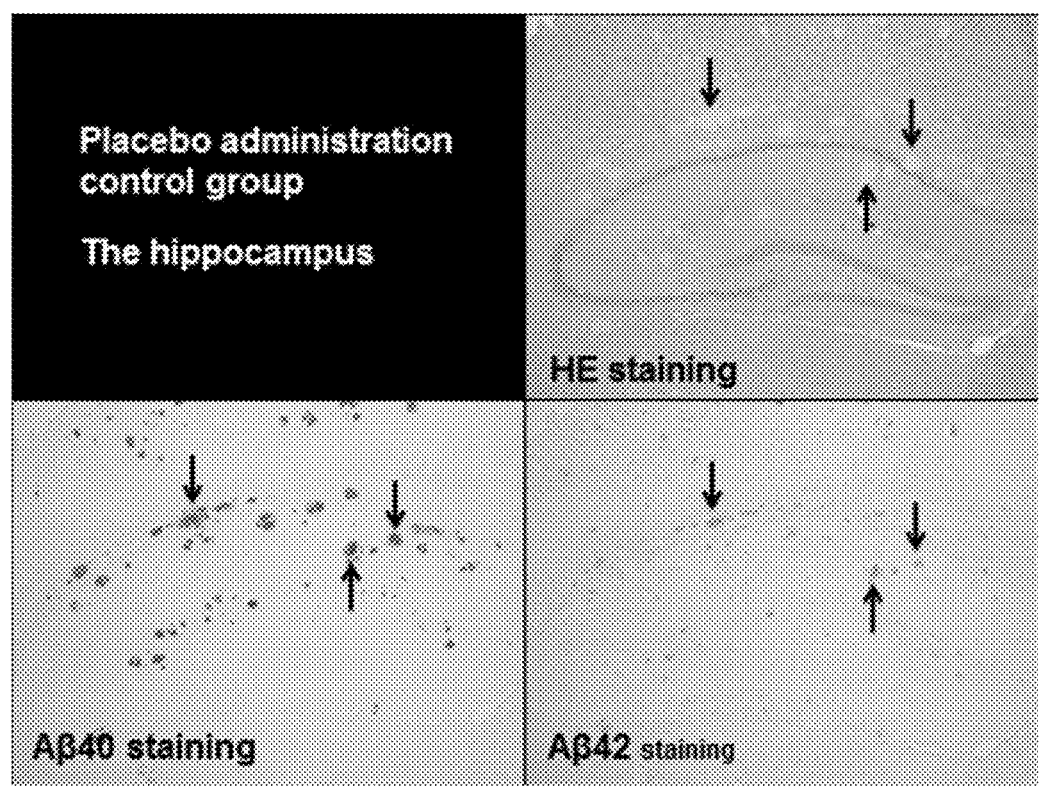
FIG. 5 Photographs showing results of the HE staining, Aβ40 immunostaining, and Aβ42 immunostaining of the hippocampus of the mouse of the 0.5% methylcellulose (placebo) administration control group: Positions of senile plaques are indicated with arrows. Many large-sized senile plaques can be confirmed.
Figure 6:
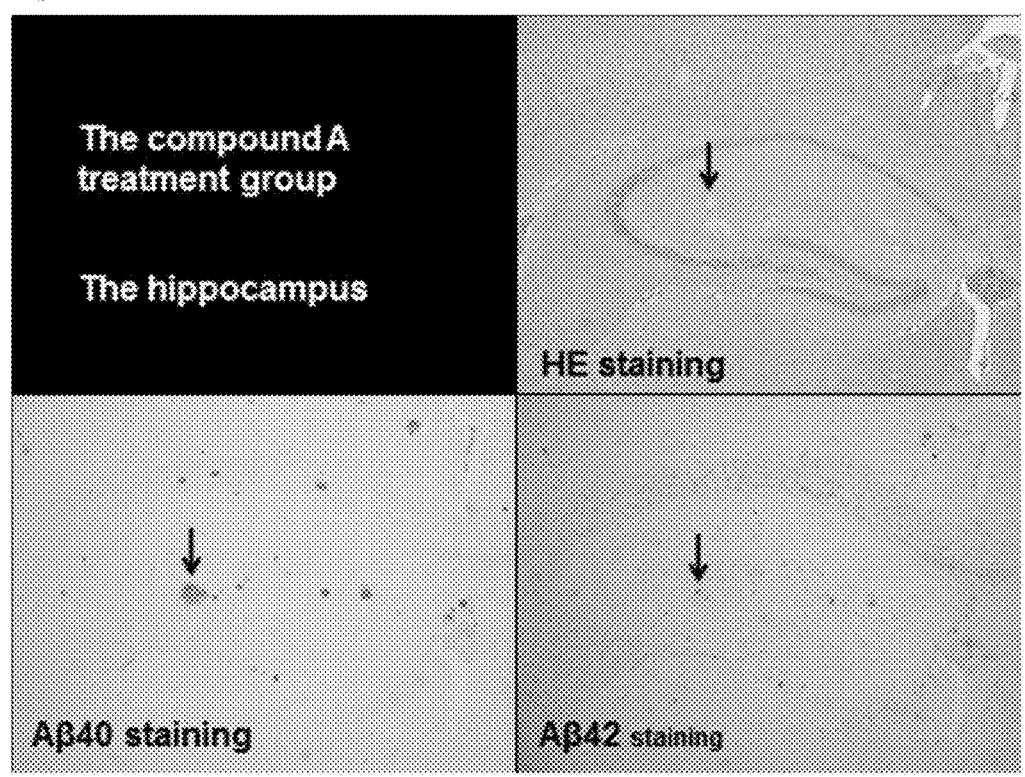
FIG. 6 Photographs showing results of the HE staining, Aβ40 immunostaining, and Aβ42 immunostaining of the hippocampus of the mouse of the compound A treatment group: Positions of senile plaques are indicated with arrows. There are clearly fewer large-sized senile plaques in the compound A treatment group compared with the 0.5% methylcellulose (placebo) administration control group.

(b) Results
1. Senile Plaque
1) Neuropathologico-Morphological Characteristics of Senile Plaque Pathological tissue samples of mammillary body coronal cut surfaces including the hippocampus in the cerebrum of the Alzheimer's disease model double transgenic mice are shown in FIGS. 5 and 6.

Senile plaques, which do not appear in the model mice younger than 700 days old and normal mice of more than 700 days old, could be easily identified in the hippocampuses of the Alzheimer's disease model double transgenic mice by HE staining. As the senile plaques that appeared in the Alzheimer's disease model double transgenic mice, there were two kinds of senile plaques distinguished on the basis of neuropathologico-morphological characteristics, i.e., senile plaques consisting of a structure having a center portion called core, which is deeply stained by the HE staining, and hallo around the core, which is lightly stained by the HE staining, and senile plaques consisting of only the hallo, which is lightly stained by the HE staining. They were the same as the senile plaques that appear in human Alzheimer's disease from the viewpoint of the HE-staining. From the viewpoint of the HE-staining, the senile plaques that appeared in the Alzheimer's disease model double transgenic mice of the former type correspond to the classical type senile plaques among the senile plaques that appear in human Alzheimer's disease, and the senile plaques of the latter type correspond to the diffuse type senile plaques among the senile plaques that appear in human Alzheimer's disease.

The senile plaques that appeared in the Alzheimer's disease model double transgenic mice and could be identified by the HE staining could be identified with either one or both of the anti-amyloid β protein_Aβ40 antibody (clone No. BA27), and anti-amyloid β protein_Aβ42 antibody (clone No. BC05). The senile plaques that appeared in the 0.5% methylcellulose administration control group (FIG. 5), and the senile plaques that appeared in the compound A treatment group (FIG. 6) were the same from the viewpoints of neuropathologico-morphology, and staining. The Aβ40 and Aβ42 immunostaining-positive senile plaques that appeared in the Alzheimer's disease model double transgenic mice of the both groups were the same as the Aβ40 and Aβ42 immunostaining-positive senile plaques that appear in human Alzheimer's disease from the viewpoints of neuropathologico-morphology, and staining.

2) Results of Quantitative Analysis of Number of Senile Plaque

The neurohistopathological characteristics of the senile plaques that appeared in the Alzheimer's disease model double tranagenic mice were the same as the neurohistopathological characteristics of the senile plaque of human Alzheimer's disease, and the neurohistopathological characteristics of the senile plaques in both the control group and the compound A treatment group were the same. Therefore, in the evaluation based on senile plaques, the effectiveness of the compound A for suppressing human Alzheimer's disease was evaluated with the results of the quantitative analysis of the number of senile plaques and size (growth degree) of the diameter thereof.

In consideration of the favorite sites of the senile plaques in the Alzheimer's disease model double transgenic mice, and on the basis of three types of HE staining, Aβ40 immunostaining, and Aβ42 immunostaining consecutively performed, senile plaques that appeared in a coronal cut surface of the mammillary body (including hippocampus and subiculum), and cerebrum coronal cut surface of entorhinal cortex (cerebral cortex including hippocampus, subiculum, and entorhinal cortex) were counted.

The data for respective cut surfaces are shown below.

Compound A (1)
Mammillary body coronal cut surface: Large-sized senile plaque 21, medium-sized senile plaque 33, and small senile plaque 113
Entorhinal cortex coronal cut surface: Large-sized senile plaque 16, medium-sized senile plaque 78, and small senile plaque 96

Compound A (2)
Mammillary body coronal cut surface: Large-sized senile plaque 12, medium-sized senile plaque 12, and small senile plaque 38
Entorhinal cortex coronal cut surface: Large-sized senile plaque 10, medium-sized senile plaque 24, and small senile plaque 78

Compound A (3)
Mammillary body coronal cut surface: Large-sized senile plaque 12, medium-sized senile plaque 25, and small senile plaque 106
Entorhinal cortex coronal cut surface: Large-sized senile plaque 11, medium-sized senile plaque 31, and small senile plaque 110

Compound A (4)
Mammillary body coronal cut surface: Large-sized senile plaque 5, medium-sized senile plaque 30, and small senile plaque 130
Entorhinal cortex coronal cut surface: Large-sized senile plaque 2, medium-sized senile plaque 14, and small senile plaque 164

Control (1)
Mammillary body coronal cut surface: Large-sized senile plaque 8, medium-sized senile plaque 27, and small senile plaque 42
Entorhinal cortex coronal cut surface: Large-sized senile plaque 13, medium-sized senile plaque 36, and small senile plaque 76

Control (2)
Mammillary body coronal cut surface: Large-sized senile plaque 29, medium-sized senile plaque 37, and small senile plaque 108
Entorhinal cortex coronal cut surface: Large-sized senile plaque 21, medium-sized senile plaque 45, and small senile plaque 102

Control (3)
Mammillary body coronal cut surface: Large-sized senile plaque 40, medium-sized senile plaque 66, and small senile plaque 139
Entorhinal cortex coronal cut surface: Large-sized senile plaque 42, medium-sized senile plaque 65, and small senile plaque, 124

Control (4)
Mammillary body coronal cut surface: Large-sized senile plaque 35, medium-sized senile plaque 46, and small senile plaque 63
Entorhinal cortex coronal cut surface: Large-sized senile plaque 27, medium-sized senile plaque 32, and small senile plaque 52

Per one cerebrum coronal cut surface, the numbers of the large-sized senile plaques were 11.1±5.9 for the compound A treatment group, and 26.9±12.3 for the control group, the numbers of the medium-sized senile plaques were 30.9±20.5 for the compound A treatment group, and 44.3±14.5 for the control group, and the numbers of the small-sized senile plaques were 104.4±36.8 for the compound A treatment group, and 88.3±35.2 for the control group.

Figure 7:
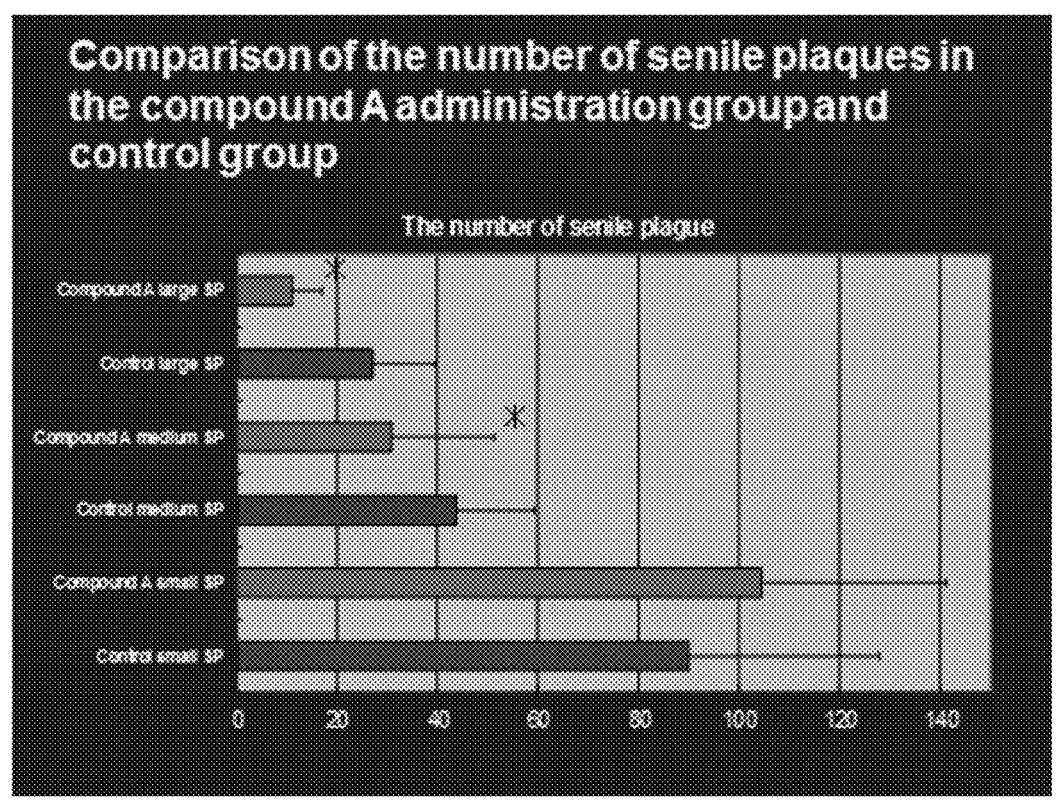
FIG. 7 A graph showing numbers of senile plaques in the compound A administration group and the control group based on the size of senile plaque. As for the size of senile plaque, senile plaques having a diameter of 100 µm or larger were classified as large-sized senile plaques (large-sized SPs), those having a diameter of 50 µm or smaller as small-sized senile plaques (small-sized SPs), and those having a diameter between 50 µm and 100 µm as medium-sized senile plaques (medium SPs). In the graph, the indication "Compound A large SP" means the number of large-sized senile plaques of the group in which the compound A was administered, "Control large SP" means the number of large-sized senile plaques of the group in which the placebo was administered, "Compound A medium SP" means the number of the medium-sized senile plaques of the group in which the compound A was administered, "Control medium SP" means the number of the medium-sized senile plaques of the group in which the placebo was administered, "Compound A small SP" means the number of the small-sized senile plaques of the group in which the compound A was administered, and "Control small SP" means the number of small-sized senile plaques of the group in which the placebo was administered. It can be seen that formation of large-sized senile plaques and medium-sized senile plaques was especially suppressed in the compound A administration group (*$p<0.05$), and growth (=enlargement) of senile plaques is significantly suppressed by the administration of the compound A.

As a result of statistical analysis, in comparison of the numbers of large-sized senile plaques and the numbers of medium-sized senile plaques, the numbers of senile plaques of the compound A treatment group were significantly smaller compared with the control group (p=0.013 and p=0.036, Mann-Whitney U test). Any significant difference was not observed between the numbers of small senile plaques (p=0.400, Mann-Whitney U test) (FIG. 7).

2. Neurofibrillary Tangle

Figure 8:
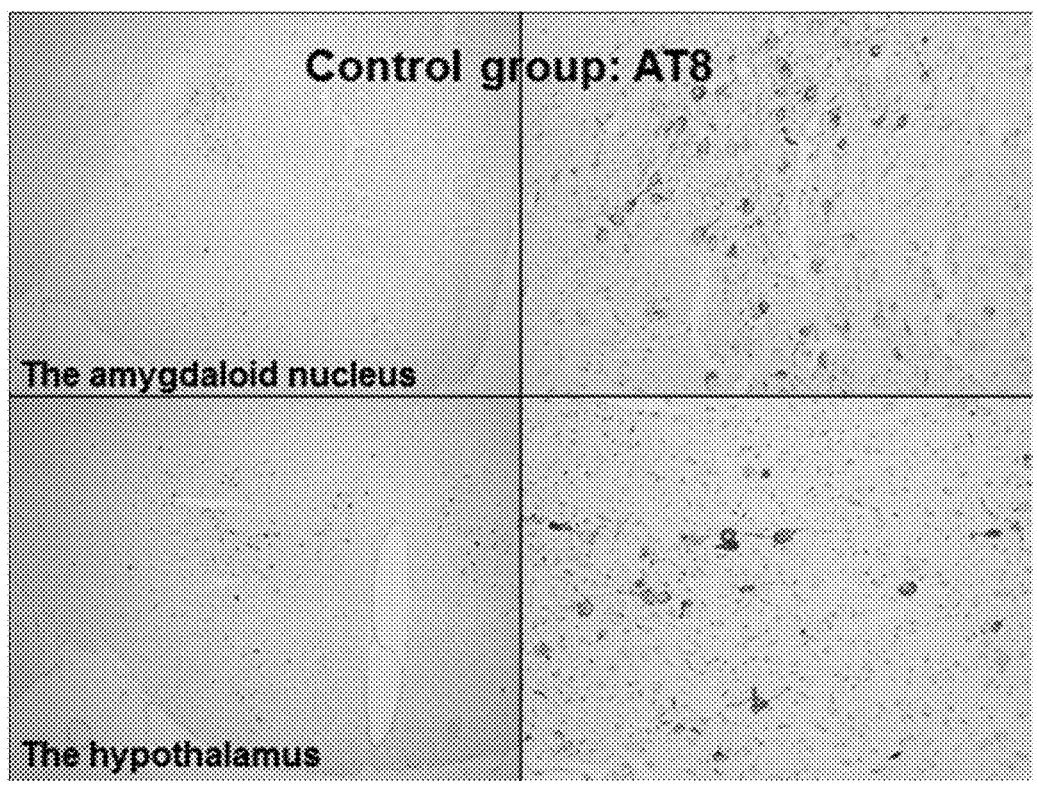
FIG. 8 Photographs showing results of AT8 immunostaining for identifying the phosphorylated tau protein, which is a core protein of the neurofibrillary tangles, in the amygdaloid nucleus and hypothalamus performed for the control group: The photographs on the left side show weakly enlarged images of parts of the amygdaloid nucleus and hypothalamus, and the photographs on the right side show strongly enlarged images of parts of the amygdaloid nucleus and hypothalamus. Many nerve cells having AT8 immunostaining-strongly positive neurofibrillary tangles are observed in the amygdaloid nucleus and hypothalamus.
Figure 9:
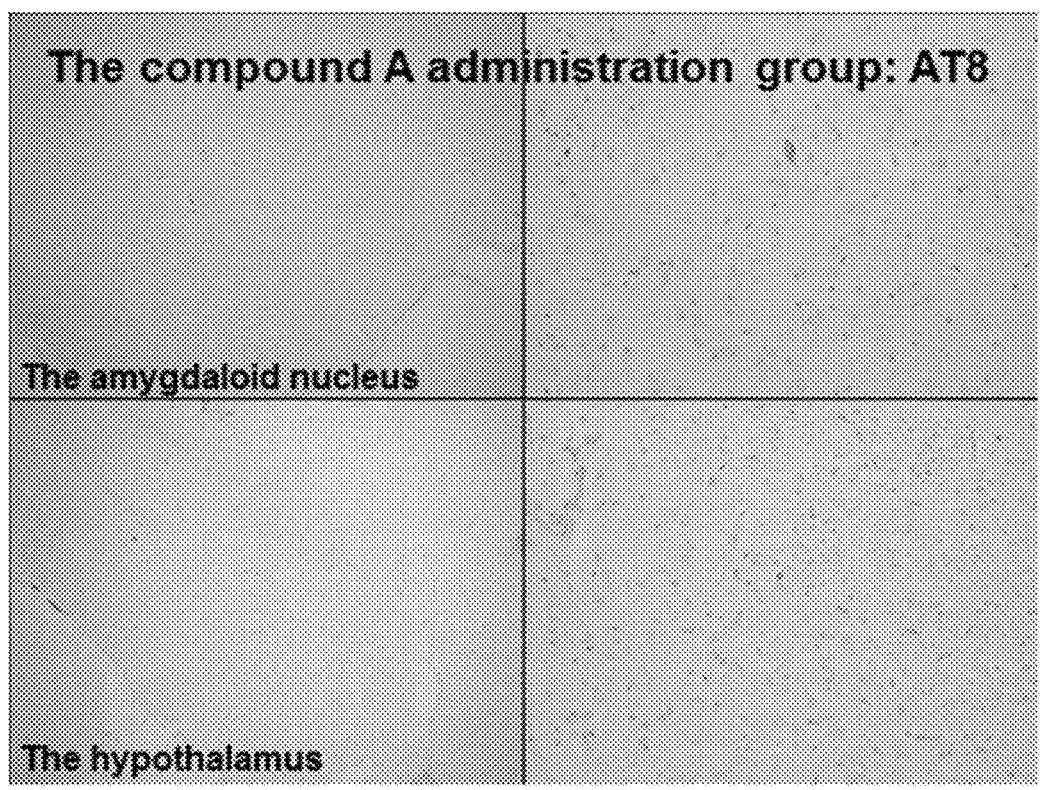
FIG. 9 Photographs showing results of AT8 immunostaining in the amygdaloid nucleus and hypothalamus performed for the compound A administration group: The photographs on the left side show weakly enlarged images of parts of the amygdaloid nucleus and hypothalamus, and the photographs on the right side show strongly enlarged images of parts of the amygdaloid nucleus and hypothalamus. Although nerve cells having AT8 immunostaining-positive neurofibrillary tangles are observed in the amygdaloid nucleus and hypothalamus, the number of AT8 immunostaining-positive nerve cells of the compound A administration group is fewer than that of the control group.

1) Neuropathologico-morphological characteristics of neurofibrillary tangles Pathological tissue samples of cerebrum coronal cut surfaces including the amygdaloid nucleus and hypothalamus in the cerebrums of the Alzheimer's disease model double transgenic mice are shown in FIGS. 8 and 9.

Neurofibrillary tangles, which do not appear in the model mice not older than 700 days old and normal mice of 700 days or more old, could be easily identified in the hypothalamus and amygdaloid nucleus of the Alzheimer's disease model double transgenic mice by the AT8 immunostaining, which identifies the phosphorylated tau protein as the core protein of neurofibrillary tangles. The nerve cells having AT8 immunostaining-positive neurofibrillary tangles that appeared in the mice of the 0.5% methylcellulose administration control group (FIG. 8), and the nerve cells having AT8 immunostaining-positive neurofibrillary tangles that appeared in the mice of the compound A administration treatment group (FIG. 9) were the same from the viewpoints of neuropathologico-morphology and staining. Further, the nerve cells having AT8 immunostaining-positive neurofibrillary tangles that appeared in both the groups were the same as nerve cells having AT8 immunostaining-positive neurofibrillary tangles that appear in human Alzheimer's disease patients from the viewpoints of neuropathologico-morphology and staining.

It was difficult to identify the AT8 immunostaining-positive neurofibrillary tangles observed in the Alzheimer's disease model double transgenic mice by the HE staining as routine staining. On the other hand, as for the AT8 immunostaining-positive neurofibrillary tangles that appear in human Alzheimer's disease patients, a part of the nerve cells having AT8 immunostaining-positive neurofibrillary tangles is a structure that can be identified only by HE staining for neuropathologists well informed of human Alzheimer's disease. On the basis of this empirical fact, in HE-staining, difference was observed between the AT8 immunostaining-positive neurofibrillary tangles that appeared in the Alzheimer's disease model double transgenic mice and the AT8 immunostaining-positive neurofibrillary tangles that appear in human Alzheimer's disease patients from the viewpoint of the aforementioned finding. However, on the basis of the fact that, as for both the AT8 immunostaining-positive neurofibrillary tangles that appear in human Alzheimer's disease patients, and the AT8 immunostaining-positive neurofibrillary tangles that appeared in the Alzheimer's disease model double transgenic mice, the AT8 immunostaining showed markedly higher sensitivity for detection of the neurofibrillary tangles compared with HE staining, the nerve cells having neurofibrillary tangles were evaluated on the basis of AT8 immunostaining-positive neurofibrillary tangles.

2) Quantitative Analysis of Number of Nerve Cells Having AT8 Immunostaining-Positive Neurofibrillary Tangles The neurohistopathological characteristics of the nerve cells having AT8 immunostaining-positive neurofibrillary tangles observed in the Alzheimer's disease model double transgenic mice are the same as the neurohistopathological characteristics of nerve cells having AT8 immunostaining-positive neurofibrillary tangles observed in human Alzheimer's disease patients, and the neurohistopathological characteristics of the nerve cells having AT8 immunostaining-positive neurofibrillary tangles observed in both the control group and the compound A treatment group were the same. On the basis of these results, as for the AT8 immunostaining-positive neurofibrillary tangles, effectiveness of the compound A for suppressing human Alzheimer's disease was evaluated on the basis of the quantitative analysis results of the nerve cells having AT8 immunostaining-positive neurofibrillary tangles.

In consideration of the favorite sites of the nerve cells having the AT8 immunostaining-positive neurofibrillary tangles observed in the Alzheimer's disease model double transgenic mice, nerve cells having AT8 immunostaining-positive neurofibrillary tangles that appeared on cerebrum coronal cut surfaces including the hypothalamus, and cerebrum coronal cut surface in which the amygdaloid nucleus showed the maximum diameter were counted.

The data for the respective cut surfaces are shown below.

Compound A (1)
Hypothalamus coronal cut surface: 149
Amygdaloid nucleus maximum diameter coronal cut surface: 103
Compound A (2)
Hypothalamus coronal cut surface: 119
Amygdaloid nucleus maximum diameter coronal cut surface: 175
Compound A (3)
Hypothalamus coronal cut surface: 26
Amygdaloid nucleus maximum diameter coronal cut surface: 13
Compound A (4)
Hypothalamus coronal cut surface: 13
Amygdaloid nucleus maximum diameter coronal cut surface: 18
Control (1)
Hypothalamus coronal cut surface: 259
Amygdaloid nucleus maximum diameter coronal cut surface: 237
Control (2)
Hypothalamus coronal cut surface: 204
Amygdaloid nucleus maximum diameter coronal cut surface: 153
Control (3)
Hypothalamus coronal cut surface: 283
Amygdaloid nucleus maximum diameter coronal cut surface: 198
Control (4)
Hypothalamus coronal cut surface: 180
Amygdaloid nucleus maximum diameter coronal cut surface: 165

The number of the nerve cells having AT8 immunostaining-positive neurofibrillary tangles per one cerebrum coronal cut surface for the compound A treatment group was 77.0±67.1, and the number of the nerve cells having AT8 immunostaining-positive neurofibrillary tangles per one cerebrum coronal cut surface for the 0.5% methylcellulose administration control group was 209.9±46.0.

Figure 10:
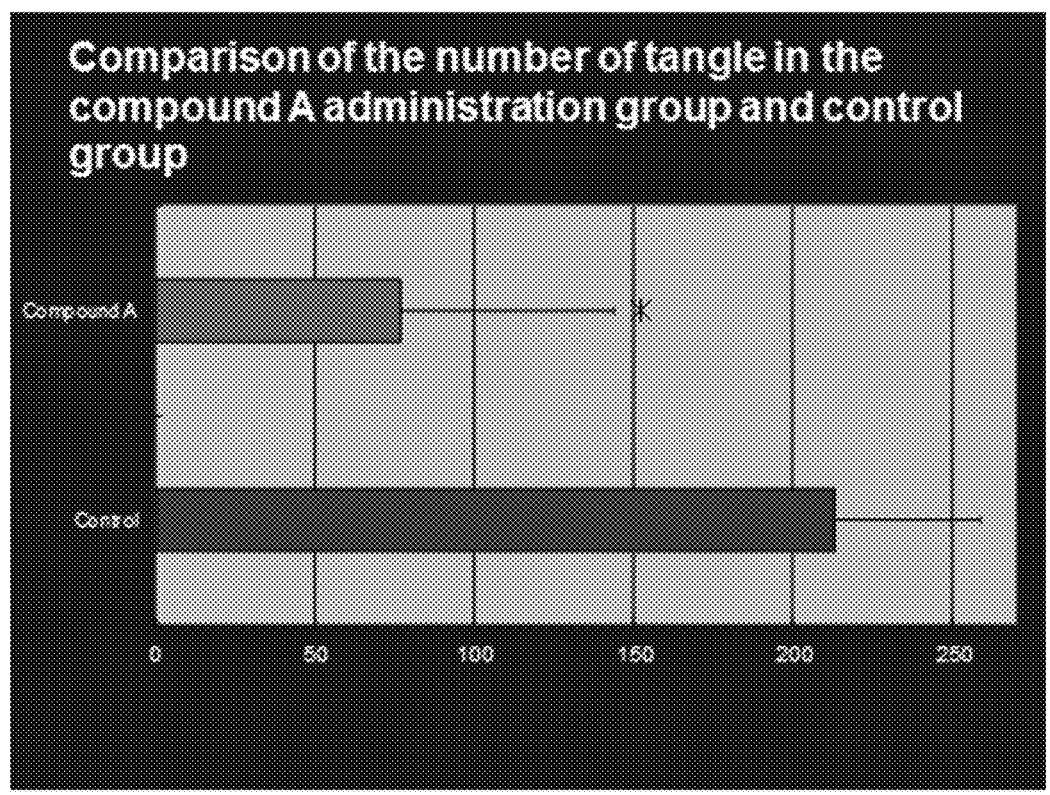
FIG. 10 A graph showing comparison of the numbers of nerve cells having AT8 immunostaining-positive neurofibrillary tangles (tangle numbers) in the compound A administration group and the control group: The number of nerve cells having AT8 immunostaining-positive neurofibrillary tangles (tangle number) of the compound A administration group was 36% of that of the control group. In the compound A treatment group, the number of the nerve cells having AT8 immunostaining-positive neurofibrillary tangles was significantly lower (*$p<0.05$), and thus it was demonstrated that the neurofibrillary tangles as one of the remarkable features (hallmarks) of the neurohistopathological findings of Alzheimer's disease are significantly suppressed by administration of the compound A.

As a result of statistical analysis, it was found that the number of nerve cells having AT8 immunostaining-positive neurofibrillary tangles was significantly smaller in the compound A treatment group compared with the control group (p=0.016, Mann-Whitney U test) (FIG. 10).

As described above, it was demonstrated that the compound A, which is a selective inhibitor of xanthine oxioreductase, markedly suppresses advance of Alzheimer's disease in model mice based on the causative genes of the disease, as shown by the pathological findings thereof. That is, it was found that the compound A, which is a selective inhibitor of xanthine oxioreductase, significantly suppresses the numbers of large-sized senile plaques and medium-sized senile plaques in Alzheimer's disease model mice through oral administration thereof. It was also found that the compound A markedly suppresses neurofibrillary tangles, i.e., accumulation of the phosphorylated tau protein in nerve cells, in Alzheimer's disease model mice through oral administration thereof.

What is claimed is:

1. A method of suppressing the formation of senile plaques and/or neurofibrillary tangles and/or decreasing the number of senile plaques and/or neurofibrillary tangles, the method comprising administering to a subject in need of treatment thereof a therapeutically effective amount of a compound represented by the following formula (I), a tautomer of the compound, a stereoisomer of the compound, a pharmaceutically acceptable salt of the compound, or a solvate of the compound as an active ingredient:

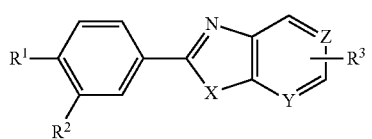

(I)

wherein,

R$^1$ represents a morpholine group, a 1-methylpiperazine group, a thiomorpholine group, —OR$^4$, or —S(O)$_n$R$^6$, where R$^4$ represents an allyl group, a pyridyl group, an alkyl group having 1 to 8 carbon atoms, or an aryl group having 6 to 10 carbon atoms, which may have one or more substituents, the substituent(s) being one or more of an amino group, a carboxyl group, a halogen atom, a hydroxy group, a nitro group, and/or a cyano group, R$^6$ represents an aryl group having 6 to 10 carbon atoms, which may have one or more substituents, the substituent(s) being one or more of a carboxyl group, a halogen atom, a hydroxy group, a nitro group, a cyano group, and/or an amino group, and n represents an integer of 0 to 2, R$^2$ represents a halogen atom, a nitro group, a cyano group, or CO$_2$R$^7$, where R$^7$ represents a hydrogen atom, an alkyl group having 1 to 8 carbon atoms, an aralkyl group, wherein the aryl moiety of the aralkyl group has 6 to 10 carbon atoms and the alkyl moiety of the aralkyl group has 1 to 4 carbon atoms, or an aryl group having 6 to 10 carbon atoms, which may have one or more substituents, the substituent(s) being one or more of a halogen atom, a hydroxy group, a nitro group, a cyano group, and/or an amino group, R$^3$ represents a hydrogen atom, a halogen atom, a hydroxy group, an amino group, or CO$_2$R$^8$, where R$^8$ has the same meaning as that of R$^7$, X represents NR$^{11}$, an oxygen atom, or a sulfur atom, where R$^{11}$ represents a hydrogen atom, and Y and Z represent a nitrogen atom.

2. The method according to claim 1, wherein R$^1$ is a morpholine group, a 1-methyl piperazine group, a thiomorpholine group, an alkoxy group having 1 to 5 carbon atoms, a phenylthio group, an allyloxy group, a pyridyloxy group, or a phenoxy group, which may have one or more substituents, the substituent(s) being one or more of halogen atom, a hydroxy group, a nitro group, and/or a cyano group.

3. The method according to claim 1, wherein R$^2$ is a nitro group, a cyano group, a halogen atom, or a carboxyl group.

4. The method according to claim 1 wherein R$^3$ is a hydrogen atom, an amino group, a hydroxy group, a halogen atom, or a carboxyl group.

5. The method according to claim 1, wherein X is an oxygen atom or a sulfur atom.

6. The method according to claim 1, wherein R$^1$ is a morpholine group, a 1-methylpiperazine group, a thiomorpholine group, an alkoxy group having 1 to 5 carbon atoms, a phenylthio group, an allyloxy group, a pyridyloxy group, or a phenoxy group, which may have one or more substituents, the substituent(s) being one or more of an amino group, a carboxyl group, a halogen atom, a hydroxy group, a nitro group, and/or a cyano group, R$^2$ is a nitro group, a cyano group, a halogen atom, or a carboxyl group, R$^3$ is a hydrogen atom, an amino group, a hydroxy group, a halogen atom, or a carboxyl group, X is an oxygen atom, a sulfur atom, or NH, and both Y and Z are nitrogen atoms.

7. The method according to claim 1, wherein R$^1$ is an alkoxy group having 1 to 5 carbon atoms, or a phenoxy group, which may have a substituent selected from the group consisting of a halogen atom, a hydroxy group, a nitro group, and a cyano group, R$^2$ is a nitro group, a cyano group, a halogen atom, or a carboxyl group, R$^3$ is a hydrogen atom, an amino group, a hydroxy group, a halogen atom, or a carboxyl group, X is an oxygen atom, or a sulfur atom, and both Y and Z are nitrogen atoms.

8. The method according to claim 1, wherein R$^1$ is an alkoxy group having 1 to 5 carbon atoms, or a phenoxy group, R$^2$ is a cyano group, R$^3$ is a hydroxy group, X is an oxygen atom, or a sulfur atom, and both Y and Z are nitrogen atoms.

9. The method according to claim 1, wherein the compound is:
(1) 5-(7-hydroxyoxazolo[5,4-d]pyrimidin-2-yl)-2-methoxy-benzonitrile;
(2) 5-(7-hydroxythiazolo[5,4-d]pyrimidin-2-yl)-2-phenoxy-benzonitrile;
(3) 2-[4-(2-fluorophenoxy)-3-nitro-phenyl]thiazolo[5,4-d]pyrimidin-7-ol;
(6) 2-[4-(4-fluorophenoxy)-3-cyanophenyl]thiazolo[5,4-d]pyrimidine;
(7) 2-(3-cyano-4-phenoxyphenyl)thiazolo[5,4-d]pyrimidine;
(8) 2-[3-cyano-4-(3-pyridyloxy)phenyl]thiazolo[5,4-d]pyrimidine;
(9) 8-[3-cyano-4-(4-fluorophenoxy)phenyl]-9H-purine;
(10) 2-[3-cyano-4-(2-fluorophenoxy)phenyl]thiazolo[5,4-d]pyrimidine;
(11) 2-[3-cyano-4-(3-fluorophenoxy)phenyl]thiazolo[5,4-d]pyrimidine;
(12) 2-[3-cyano-4-(4-fluorophenylthio)phenyl]thiazolo[5,4-d]pyrimidine;
(13) 2-[3-cyano-4-(2-hydroxyphenoxy)phenyl]thiazolo[5,4-d]pyrimidine;
(14) 2-[4-(4-chlorophenyloxy)-3-cyanophenyl]thiazolo[5,4-d]pyrimidine;
(15) 2-[3-cyano-4-(2-fluorophenylthio)phenyl]thiazolo[5,4-d]pyrimidine;
(16) 2-(3-cyano-4-phenylthiophenyl)thiazolo[5,4-d]pyrimidine;

(17) 2-(4-allyloxy-3-cyanophenyl)thiazolo[5,4-d]pyrimidine;
(18) 2-(3-cyano-4-morpholin-4-ylphenyl)thiazolo[5,4-d]pyrimidine;
(19) 2-[3-cyano-4-(4-methyl-1-piperazinyl)phenyl]thiazolo[5,4-d]pyrimidine;
(20) 2-[4-(3-chlorophenyloxy)-3-cyanophenyl]thiazolo[5,4-d]pyrimidine;
(21) 2-[3-cyano-4-(thiomorpholin-4-yl)phenyl]thiazolo[5,4-d]pyrimidine;
(22) 2-[4-(2-chlorophenyloxy)-3-cyanophenyl]thiazolo[5,4-d]pyrimidine;
(23) 2-[3-cyano-4-(4-fluorophenoxy)phenyl]oxazolo[5,4-d]pyrimidine;
(24) 2-[3-cyano-4-(3-fluorophenylthio)phenyl]thiazolo[5,4-d]pyrimidine;
(25) 2-[4-(2-aminophenoxy)-3-cyanophenyl]thiazolo[5,4-d]pyrimidine;
(27) 2-[3-cyano-4-(4-hydroxyphenoxy)phenyl]thiazolo[5,4-d]pyrimidine; or
(28) 2-[3-cyano-4-(2-hydroxycarbonylphenoxy)phenyl]thiazolo[5,4-d]pyrimidine; or
a pharmaceutically acceptable salt of any one of compounds (1) to (3), (6) to (25), (27), or (28);
a tautomer of any one of compounds (1) to (3), (6) to (25), (27), or (28);
a stereoisomer of any one of compounds (1) to (3), (6) to (25), (27), or (28); or
a solvate of any one of compounds (1) to (3), (6) to (25), (27), or (28).

10. The method according to claim 1, wherein the subject has been diagnosed with dementia associated with senile plaques and/or neurofibrillary tangles.

11. The method according to claim 1, wherein the subject has been diagnosed with Alzheimer type dementia.

12. A method of treating Alzheimer type dementia, the method comprising administering to a subject in need of treatment thereof a therapeutically effective amount of a compound represented by the following formula (I), a tautomer of the compound, a stereoisomer of the compound, a pharmaceutically acceptable salt of the compound, or a solvate of the compound as an active ingredient:

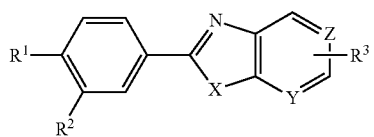
(I)

wherein,
$R^1$ represents a morpholine group, a 1-methylpiperazine group, a thiomorpholine group, —$OR^4$, or —$S(O)_nR^6$, where $R^4$ represents an allyl group, a pyridyl group, an alkyl group having 1 to 8 carbon atoms, or an aryl group having 6 to 10 carbon atoms, which may have one or more substituents, the substituent(s) being one or more of an amino group, a carboxyl group, a halogen atom, a hydroxy group, a nitro group, and/or a cyano group, $R^6$ represent an aryl group having 6 to 10 carbon atoms, which may have one or more substituents, the substituent(s) being one or more of a carboxyl group, a halogen atom, a hydroxy group, a nitro group, a cyano group, and/or an amino group as a substituent, and n represents an integer of 0 to 2, $R^2$ represents a halogen atom, a nitro group, a cyano group, or $CO_2R^7$, where $R^7$ represents a hydrogen atom, an alkyl group having 1 to 8 carbon atoms, an aralkyl group, wherein the aryl moiety of the aralkyl group has 6 to 10 carbon atoms and the alkyl moiety of the aralkyl group has 1 to 4 carbon atoms, or an aryl group having 6 to 10 carbon atoms, which may have one or more substituents, the substituent(s) being one or more of a halogen atom, a hydroxy group, a nitro group, a cyano group, and/or an amino group, $R^3$ represents a hydrogen atom, a halogen atom, a hydroxy group, an amino group, or $CO_2R^8$, where $R^8$ has the same meaning as that of $R^7$, X represents $NR^{11}$, an oxygen atom, or a sulfur atom, where $R^{11}$ represents a hydrogen atom, and Y and Z represent a nitrogen atom.

13. The method according to claim 12, wherein $R^1$ is a morpholine group, a 1-methyl piperazine group, a thiomorpholine group, an alkoxy group having 1 to 5 carbon atoms, a phenylthio group, an allyloxy group, a pyridyloxy group, or a phenoxy group, which may have one or more substituents, the substituent(s) being one or more of a halogen atom, a hydroxy group, a nitro group, and/or a cyano group.

14. The method according to claim 12, wherein $R^2$ is a nitro group, a cyano group, a halogen atom, or a carboxyl group.

15. The method according to claim 12, Wherein $R^3$ is a hydrogen atom, an amino group, a hydroxy group, a halogen atom, or a carboxyl group.

16. The method according to claim 12, wherein X is an oxygen atom or a sulfur atom.

17. The method according to claim 12, wherein $R^1$ is a morpholine group, a 1-methylpiperazine group, a thiomorpholine group, an alkoxy group having 1 to 5 carbon atoms, a phenylthio group, an allyloxy group, a pyridyloxy group, or a phenoxy group, which may have one or more substituents, the substituent(s) being one or more of an amino group, a carboxyl group, a halogen atom, a hydroxy group, a nitro group, and/or a cyano group, $R^2$ is a nitro group, a cyano group, a halogen atom, or a carboxyl group, $R^3$ is a hydrogen atom, an amino group, a hydroxy group, a halogen atom, or a carboxyl group, X is an oxygen atom, a sulfur atom, or NH, and both Y and Z are nitrogen atoms.

18. The method according to claim 12, wherein $R^1$ is an alkoxy group having 1 to 5 carbon atoms, or a phenoxy group, which may have a substituent selected from the group consisting of a halogen atom, a hydroxy group, a nitro group, and a cyano group, $R^2$ is a nitro group, a cyano group, a halogen atom, or a carboxyl group, $R^3$ is a hydrogen atom, an amino group, a hydroxy group, a halogen atom, or a carboxyl group, X is an oxygen atom, or a sulfur atom, and both Y and Z are nitrogen atoms.

19. The method according to claim 12, wherein $R^1$ is an alkoxy group having 1 to 5 carbon atoms, or a phenoxy group, $R^2$ is a cyano group, $R^3$ is a hydroxy group, X is an oxygen atom, or a sulfur atom, and both Y and Z are nitrogen atoms.

20. The method according to claim 12, wherein the compound is:
(1) 5-(7-hydroxyoxazolo[5,4-d]pyrimidin-2-yl)-2-methoxy-benzonitrile;
(2) 5-(7-hydroxythiazolo[5,4-d]pyrimidin-2-yl)-2-phenoxy-benzonitrile;
(3) 2-[4-(2-fluorophenoxy)-3-nitro-phenyl]thiazolo[5,4-d]pyrimidin-7-ol;
(6) 2-[4-(4-fluorophenoxy)-3-cyanophenyl]thiazolo[5,4-d]pyrimidine;

(7) 2-(3-cyano-4-phenoxyphenyl)thiazolo[5,4-d]pyrimidine;
(8) 2-[3-cyano-4-(3-pyridyloxy)phenyl]thiazolo[5,4-d]pyrimidine;
(9) 8-[3-cyano-4-(4-fluorophenoxy)phenyl]-9H-purine;
(10) 2-[3-cyano-4-(2-fluorophenoxy)phenyl]thiazolo[5,4-d]pyrimidine;
(11) 2-[3-cyano-4-(3-fluorophenoxy)phenyl]thiazolo[5,4-d]pyrimidine;
(12) 2-[3-cyano-4-(4-fluorophenylthio)phenyl]thiazolo[5,4-d]pyrimidine;
(13) 2-[3-cyano-4-(2-hydroxyphenoxy)phenyl]thiazolo[5,4-d]pyrimidine;
(14) 2-[4-(4-chlorophenyloxy)-3-cyanophenyl]thiazolo[5,4-d]pyrimidine;
(15) 2-[3-cyano-4-(2-fluorophenylthio)phenyl]thiazolo[5,4-d]pyrimidine;
(16) 2-(3-cyano-4-phenylthiophenyl)thiazolo[5,4-d]pyrimidine;
(17) 2-(4-allyloxy-3-cyanophenyl)thiazolo[5,4-d]pyrimidine;
(18) 2-(3-cyano-4-morpholin-4-ylphenyl)thiazolo[5,4-d]pyrimidine;
(19) 2-[3-cyano-4-(4-methyl-1-piperazinyl)phenyl]thiazolo[5,4-d]pyrimidine;
(20) 2-[4-(3-chlorophenyloxy)-3-cyanophenyl]thiazolo[5,4-d]pyrimidine;
(21) 2-[3-cyano-4-(thiomorpholin-4-yl)phenyl]thiazolo[5,4-d]pyrimidine;
(22) 2-[4-(2-chlorophenyloxy)-3-cyanophenyl]thiazolo[5,4-d]pyrimidine;
(23) 2-[3-cyano-4-(4-fluorophenoxy)phenyl]oxazolo[5,4-d]pyrimidine;
(24) 2-[3-cyano-4-(3-fluorophenylthio)phenyl]thiazolo[5,4-d]pyrimidine;
(25) 2-[4-(2-aminophenoxy)-3-cyanophenyl]thiazolo[5,4-d]pyrimidine;
(27) 2-[3-cyano-4-(4-hydroxyphenoxy)phenyl]thiazolo[5,4-d]pyrimidine; or
(28) 2-[3-cyano-4-(2-hydroxycarbonylphenoxy)phenyl]thiazolo[5,4-d]pyrimidine; or
a pharmaceutically acceptable salt of any one of compounds (1) to (3), (6) to (25), (27),or (28);
a tautomer of any one of compounds (1) to (3), (6) to (25), (27), or (28);
a stereoisomer of any one of compounds (1) to (3),(6) to (25),(27), or (28); or
a solvate of any one of compounds (1) to (3), (6) to (25), (27), or (28).

21. The method according to claim 9 wherein:
the pharmaceutically acceptable salt of (8) 2-[3-cyano-4-(3-pyridyloxy)phenyl]thiazolo[5,4-d]pyrimidine is (26) 2-[3-cyano-4-(3-pyridyloxy)phenyl]thiazolo[5,4-d]pyrimidine hydrochloride;
the pharmaceutically acceptable salt of (13) 2-[3-cyano-4-(2-hydroxyphenoxy)phenyl]thiazolo[5,4-d]pyrimidine is (29) 2-[3-cyano-4-(2-hydroxyphenoxy)phenyl]thiazolo[5,4-d]pyrimidine potassium salt; or
the pharmaceutically acceptable salt of (27) 2-[3-cyano-4-(4-hydroxyphenoxy)phenyl]thiazolo[5,4-d]pyrimidine is (30) 2-[3-cyano-4-(4-hydroxyphenoxy)phenyl]thiazolo[5,4-d]pyrimidine potassium salt.

22. The method according to claim 20 wherein:
the pharmaceutically acceptable salt of (8) 2-[3-cyano-4-(3-pyridyloxy)phenyl]thiazolo[5,4-d]pyrimidine is (26) 2-[3-cyano-4-(3-pyridyloxy)phenyl]thiazolo[5,4-d]pyrimidine hydrochloride;
the pharmaceutically acceptable salt of (13) 2-[3-cyano-4-(2-hydroxyphenoxy)phenyl]thiazolo[5,4-d]pyrimidine is (29) 2[3-cyano-4-(2-hydroxyphenoxy)phenyl]thiazolo[5,4-d]pyrimidine potassium salt; or
the pharmaceutically acceptable salt of (27) 2-[3-cyano-4-(4-hydroxyphenoxy)phenyl]thiazolo[5,4-d]pyrimidine is (30) 2-[3-cyano-4-(4-hydroxyphenoxy)phenyl]thiazolo[5,4-d]pyrimidine potassium salt.

23. The method according to claim 1, wherein
$R^1$ represents a morpholine group, a 1-methylpiperazine group, a thiomorpholine group, —$OR^4$, or —$S(O)_nR^6$, where $R^4$ represents an allyl group, a pyridyl group, an alkyl group having 1 to 8 carbon atoms, or an aryl group having 6 to 10 carbon atoms, which may have a substituent selected from the group consisting of an amino group, a carboxyl group, a halogen atom, a hydroxy group, a nitro group, and a cyano group, $R^6$ represents an aryl group having 6 to 10 carbon atoms, which may have a substituent selected from the group consisting of a carboxyl group, a halogen atom, a hydroxy group, a nitro group, a cyano group, and an amino group, and n represents an integer of 0 to 2,
$R^2$ represents a halogen atom, a nitro group, a cyano group, or $CO_2R^7$, where $R^7$ represents a hydrogen atom, an alkyl group having 1 to 8 carbon atoms, an aralkyl group, wherein the aryl moiety of the aralkyl group has 6 to 10 carbon atoms and the alkyl moiety of the aralkyl group has 1 to 4 carbon atoms, or an aryl group having 6 to 10 carbon atoms, which may have which may have a substituent selected from the group consisting of a halogen atom, a hydroxy group, a nitro group, a cyano group, and an amino group,
$R^3$ represents a hydrogen atom, a halogen atom, a hydroxy group, an amino group, or $CO_2R^8$, where $R^8$ has the same meaning as that of $R^7$,
X represents $NR^{11}$, an oxygen atom, or a sulfur atom, where $R^{11}$ represents a hydrogen atom, and
Y and Z represent a nitrogen atom.

24. The method according to claim 12, wherein
$R^1$ represents a morpholine group, a 1-methylpiperazine group, a thiomorpholine group, —$OR^4$, or —$S(O)_nR^6$, where $R^4$ represents an allyl group, a pyridyl group, an alkyl group having 1 to 8 carbon atoms, or an aryl group having 6 to 10 carbon atoms, which may have a substituent selected from the group consisting of an amino group, a carboxyl group, a halogen atom, a hydroxy group, a nitro group, and a cyano group, $R^6$ represents an aryl group having 6 to 10 carbon atoms, which may have a substituent selected from the group consisting of a carboxyl group, a halogen atom, a hydroxy group, a nitro group, a cyano group, and an amino group, and n represents an integer of 0 to 2,
$R^2$ represents a halogen atom, a nitro group, a cyano group, or $CO_2R^7$, where $R^7$ represents a hydrogen atom, an alkyl group having 1 to 8 carbon atoms, an aralkyl group, wherein the aryl moiety of the aralkyl group has 6 to 10 carbon atoms and the alkyl moiety of the aralkyl group has 1 to 4 carbon atoms, or an aryl group having 6 to 10 carbon atoms, which may have which may have a substituent selected from the group consisting of a halogen atom, a hydroxy group, a nitro group, a cyano group, and an amino group,
$R^3$ represents a hydrogen atom, a halogen atom, a hydroxy group, an amino group, or $CO_2R^8$, where $R^8$ has the same meaning as that of $R^7$,
X represents $NR^{11}$, an oxygen atom, or a sulfur atom, where $R^{11}$ represents a hydrogen atom, and
Y and Z represent a nitrogen atom.

25. The method according to claim 1, wherein $R^1$ is a morpholine group, a 1-methylpiperazine group, a thiomorpholine group, an alkoxy group having 1 to 5 carbon atoms, a phenylthio group, an allyloxy group, a pyridyloxy group, or a phenoxy group, which may have a substituent selected from the group consisting of an amino group, a carboxyl group, a halogen atom, a hydroxy group, a nitro group, and/or a cyano group, $R^2$ is a nitro group, a cyano group, a halogen atom, or a carboxyl group, $R^3$ is a hydrogen atom, an amino group, a hydroxy group, a halogen atom, or a carboxyl group, X is an oxygen atom, a sulfur atom, or NH, and both Y and Z are nitrogen atoms.

26. The method according to claim 12, wherein $R^1$ is a morpholine group, a 1-methylpiperazine group, a thiomorpholine group, an alkoxy group having 1 to 5 carbon atoms, a phenylthio group, an allyloxy group, a pyridyloxy group, or a phenoxy group, which may have a substituent selected from the group consisting of an amino group, a carboxyl group, a halogen atom, a hydroxy group, a nitro group, and/or a cyano group, $R^2$ is a nitro group, a cyano group, a halogen atom, or a carboxyl group, $R^3$ is a hydrogen atom, an amino group, a hydroxy group, a halogen atom, or a carboxyl group, X is an oxygen atom, a sulfur atom, or NH, and both Y and Z are nitrogen atoms.

* * * * *